(12) United States Patent
Ferro et al.

(10) Patent No.: US 9,217,926 B2
(45) Date of Patent: Dec. 22, 2015

(54) METHOD OF PATTERNING A BASE LAYER

(71) Applicant: Bioflex Devices, Dublin (IE)

(72) Inventors: Marc Ferro, Aix en Provence (FR); George Malliaras, Fuveau (FR)

(73) Assignee: Orthogonal, Inc., Rochester, NY (US)

(*) Notice: Subject to any disclaimer, the term of this patent is extended or adjusted under 35 U.S.C. 154(b) by 0 days.

(21) Appl. No.: 14/547,735

(22) Filed: Nov. 19, 2014

(65) Prior Publication Data
US 2015/0140729 A1    May 21, 2015

Related U.S. Application Data

(60) Provisional application No. 61/906,155, filed on Nov. 19, 2013.

(51) Int. Cl.
*G03F 7/26* (2006.01)
*G03F 7/20* (2006.01)
(Continued)

(52) U.S. Cl.
CPC ............... *G03F 7/2022* (2013.01); *G03F 7/00* (2013.01); *G03F 7/0046* (2013.01); *G03F 7/30* (2013.01); *G03F 7/38* (2013.01); *H01L 51/0018* (2013.01)

(58) Field of Classification Search
CPC ......... G03F 7/0035; G03F 7/40; G03F 7/095; G03F 7/2022; G03F 7/38; G03F 7/0046; G03F 7/00; G03F 7/30; H01L 21/0273; H01L 21/0274; H01L 21/31144; H01L 51/0018; H01J 2237/31771
USPC .................. 430/322, 314, 315, 394, 324, 328
See application file for complete search history.

(56) References Cited

U.S. PATENT DOCUMENTS 8,715,478 B2    5/2014   Berggren et al.
2007/0202589 A1*  8/2007  Kikuchi et al. ............ 435/293.1
(Continued)

FOREIGN PATENT DOCUMENTS

EP     1 681 375 A2     7/2006
WO    WO 2007/030918 A1  3/2007
(Continued)

OTHER PUBLICATIONS

Seymour, J. et al., "Fabrication of Polymer Neural Probes with Subcellular Features for Reduced Tissue Encapsulation", *Proceedings of the 28th IEEE EMBS Annual International Conference*, 4606-4609 (2006).
(Continued)

*Primary Examiner* — Caleen Sullivan
(74) *Attorney, Agent, or Firm* — Merchant & Gould P.C.

(57) ABSTRACT

A method of making a structure having a patterned a base layer and useful in the fabrication of optical and electronic devices including bioelectronic devices includes, in one embodiment, the steps of: a) providing a layer of a radiation-sensitive resin; b) exposing the layer of radiation-sensitive resin to patterned radiation to form a base layer precursor having a first pattern of exposed radiation-sensitive resin and a second pattern of unexposed radiation-sensitive resin; c) providing a layer of fluoropolymer in a third pattern over the base layer precursor to form a first intermediate structure; d) treating the first intermediate structure to form a second intermediate structure; and e) selectively removing either the first or second pattern of resin by contacting the second intermediate structure with a resin developing agent, thereby forming the patterned base layer. The method is capable of providing multilayer articles having almost any shape at high resolution without the need for expensive or damaging mechanical or laser cutting.

20 Claims, 14 Drawing Sheets

(51) Int. Cl.
*H01L 51/00* (2006.01)
*G03F 7/30* (2006.01)
*G03F 7/00* (2006.01)
*G03F 7/004* (2006.01)
*G03F 7/38* (2006.01)

(56) References Cited

U.S. PATENT DOCUMENTS

2010/0289019 A1  11/2010  Katz et al.
2011/0159252 A1*  6/2011  Ober et al. ............... 428/195.1
2011/0244188 A1*  10/2011  Komoriya et al. ............ 428/156

FOREIGN PATENT DOCUMENTS

WO  WO 2008/010982 A2  1/2008
WO  WO 2009/143357 A2  11/2009

OTHER PUBLICATIONS

Huang, J. et al., "Patterning of organic devices by interlayer lithography", *J. Mater. Chem.*, 17: 1043-1049 (2007).
Khadagholy, D., et al., "High transconductance organic electrochemical transistors", *Nature Communications*, 1-13 (2013).
International Search Report and Written Opinion for Application No. PCT/IB2014/003023 mailed Apr. 23, 2015.

* cited by examiner

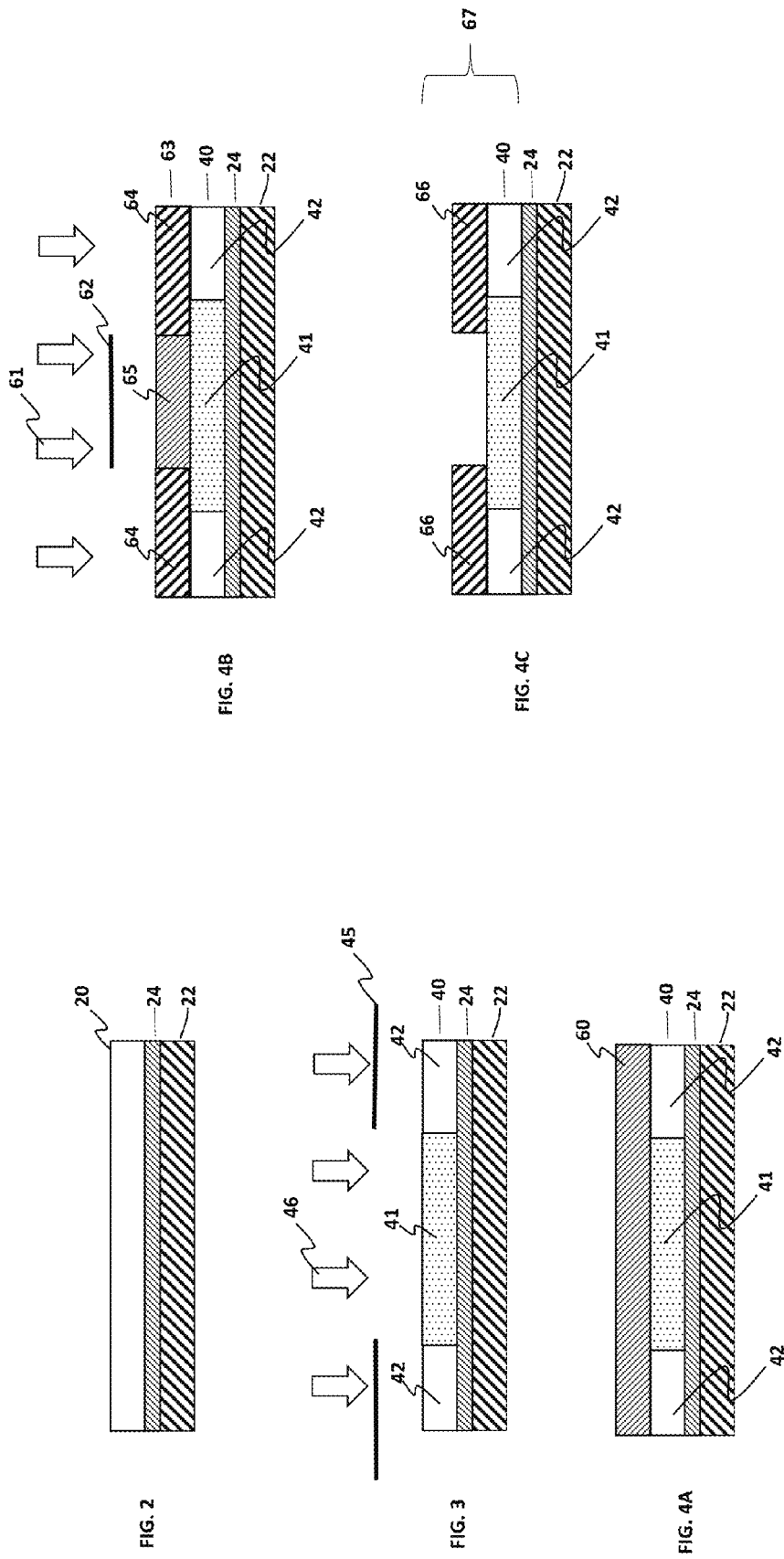

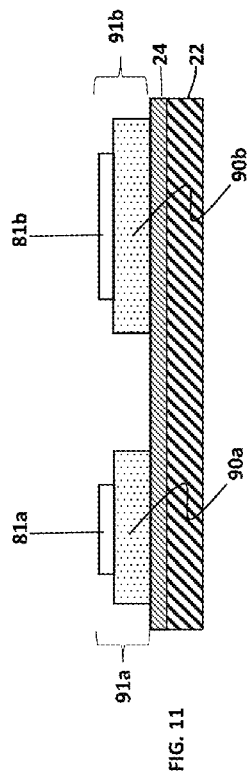
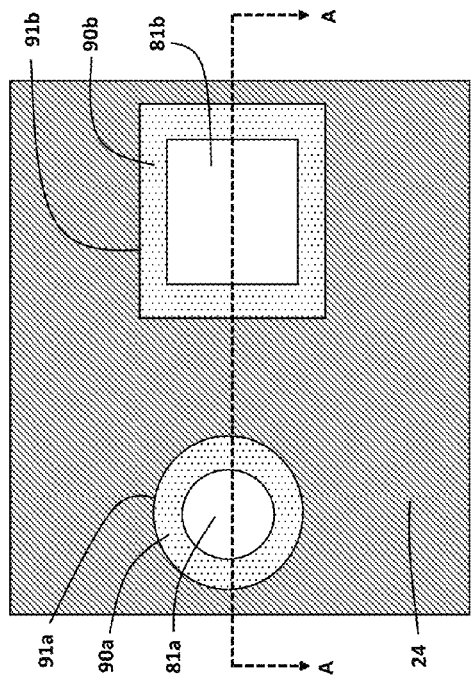
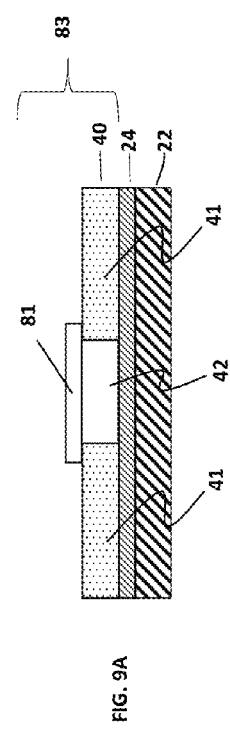
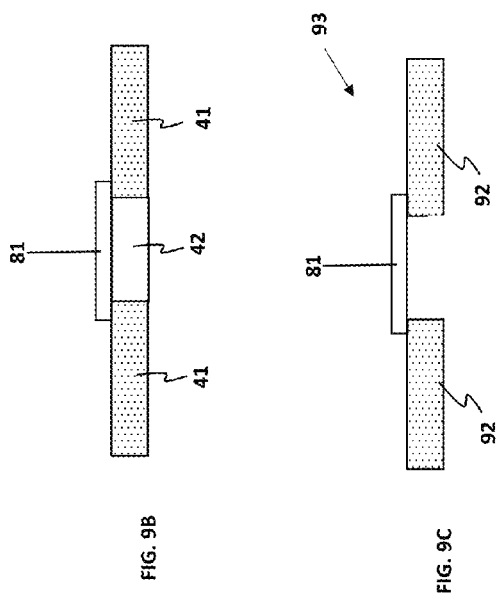
FIG. 9A  FIG. 9B  FIG. 9C  FIG. 10  FIG. 11

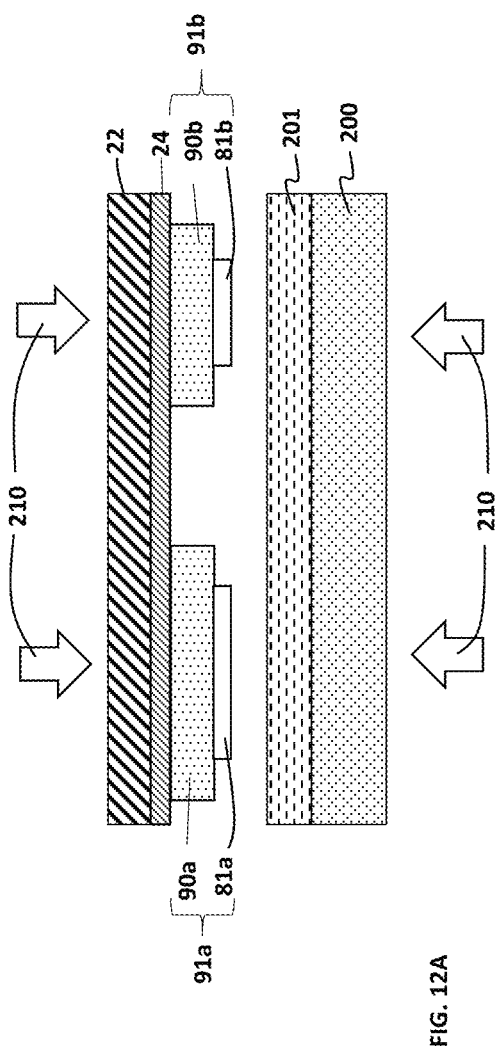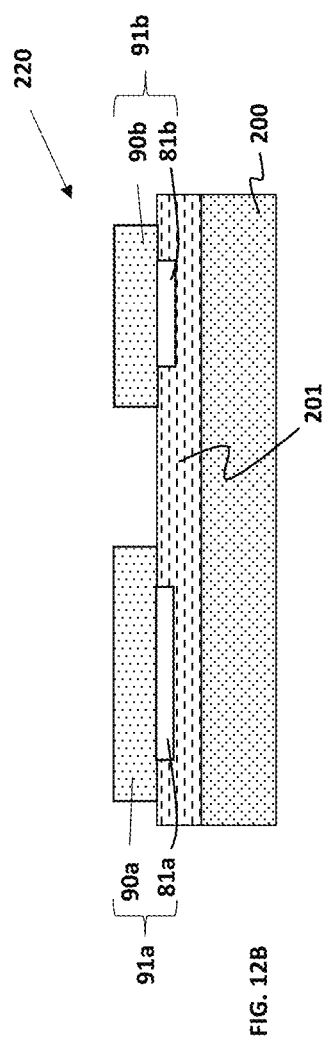
FIG. 12A
FIG. 12B

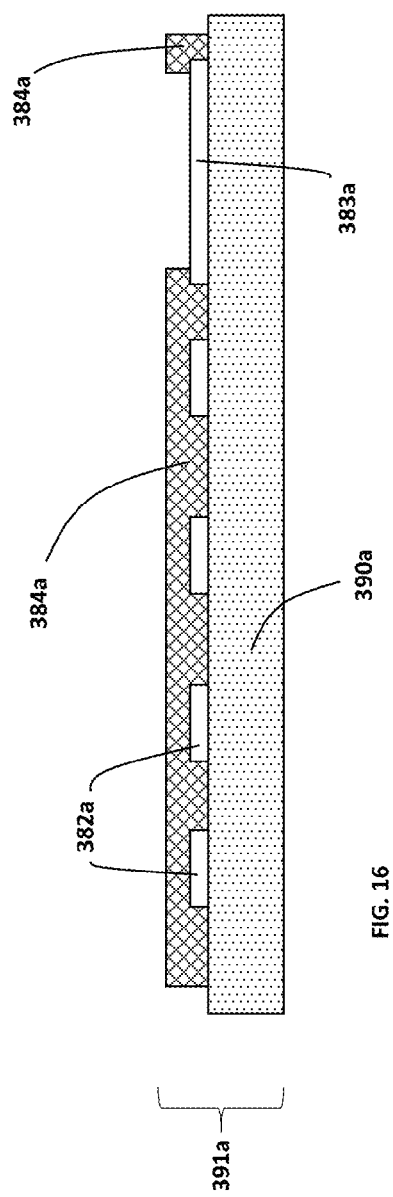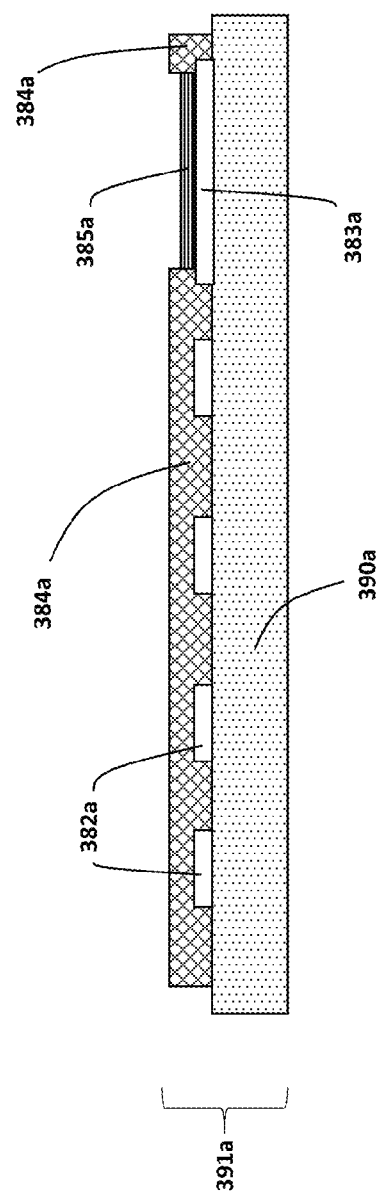

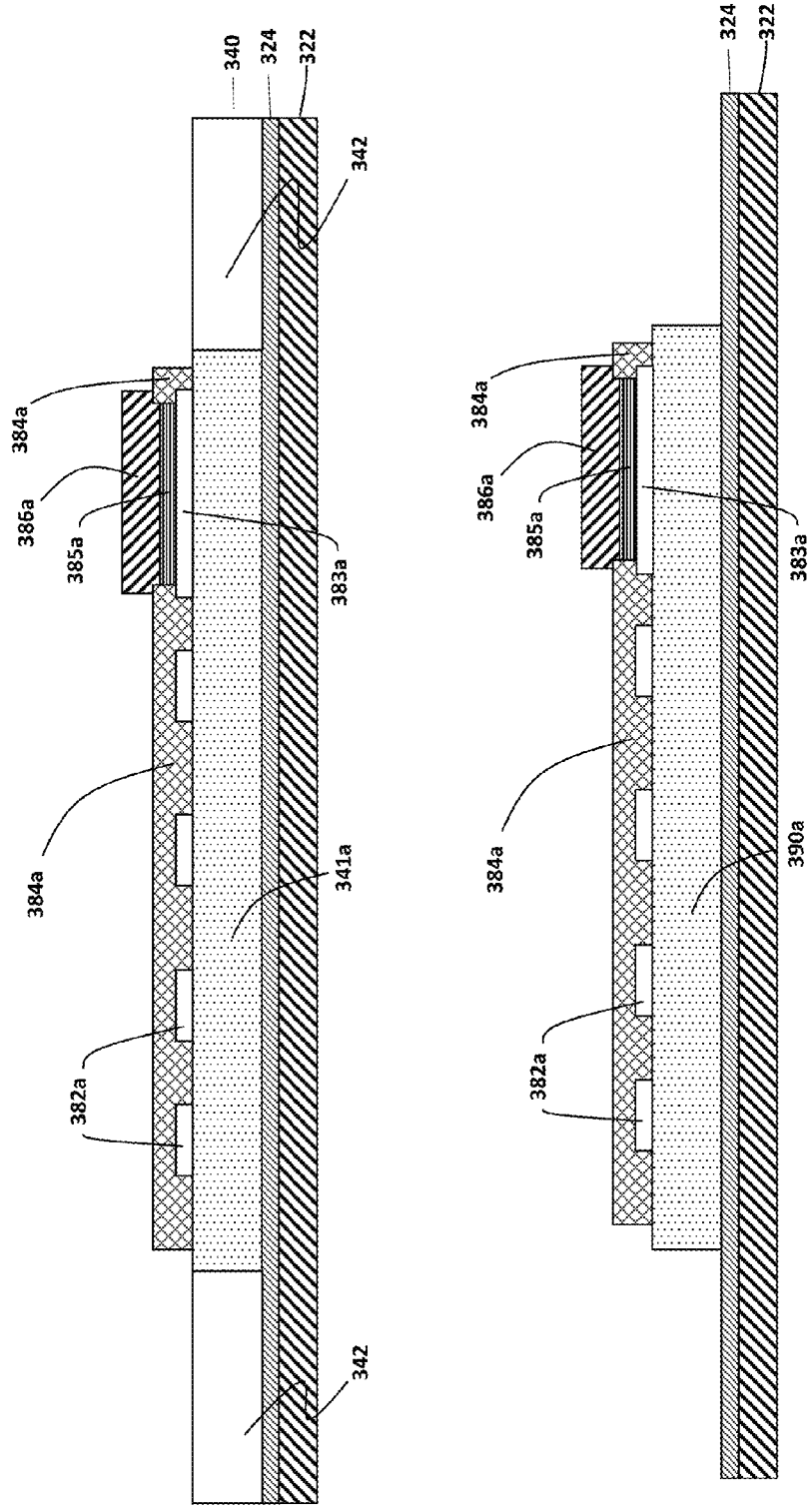

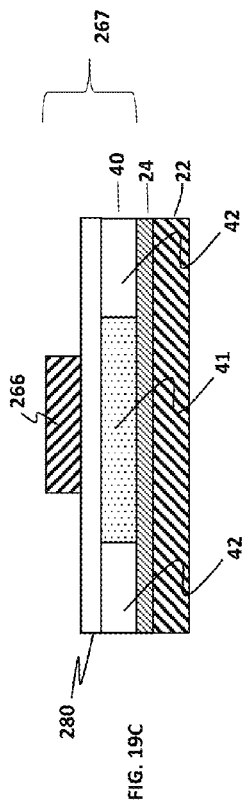
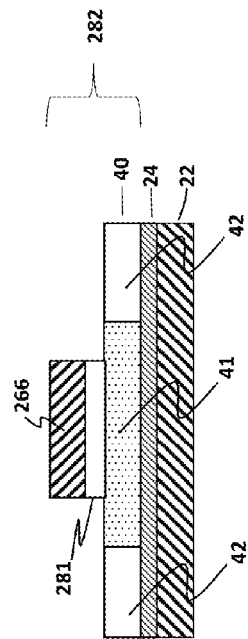
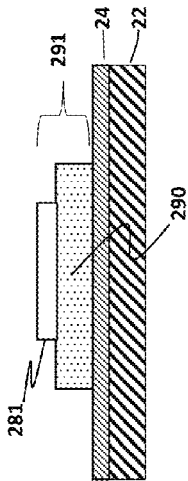
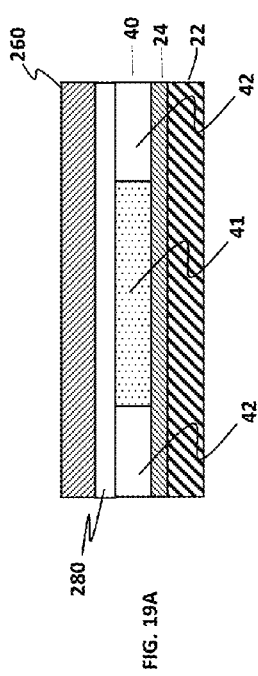
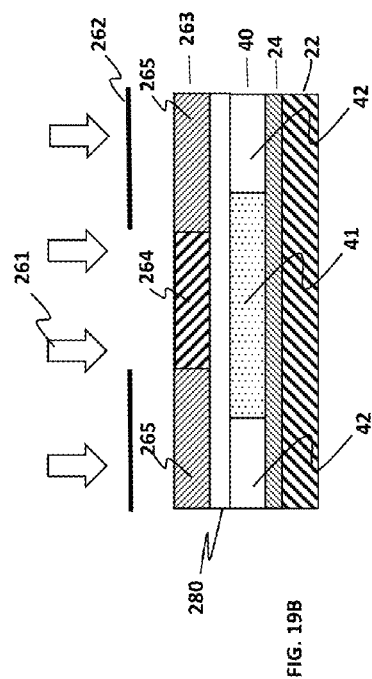

| Q1 | Q2 |
|----|----|
| Q4 | Q3 |

FIG. 21

METHOD OF PATTERNING A BASE LAYER

CROSS-REFERENCE TO RELATED APPLICATIONS

The present application claims the benefit of U.S. Provisional Application No. 61/906,155, filed Nov. 19, 2013, which is incorporated herein by reference.

BACKGROUND

The present disclosure relates to method of making a structure having a patterned a base layer. The method is particularly useful in the fabrication of optical and electronic devices including bioelectronic devices.

There are many methods available for patterning multilayer structures, e.g., in the formation of electronic, optical or mechanical components and devices. The particular method chosen depends on many factors such as dimensional tolerances, material compatibilities, throughput requirements, manufacturing costs and the like. Photolithography is a common patterning technique, used especially in the construction of microelectronic devices on flat surfaces such as glass, silicon wafers or plastic. Photolithography can provide high resolution images and may be done on a large scale. For example, electronic back planes for displays are commonly constructed using photolithography. Flat surfaces help enable uniform coating of various layers and high quality photolithographic processes. In manufacturing, a plurality of backplanes or semiconductor chips are typically constructed on a flat sheet or wafer of glass or silicon and then laser- or mechanically diced into individual backplanes or chips. This can generate unwanted dust and debris that may contaminate the devices and result in additional washing steps.

Sometimes multilayer structures or devices do not have a symmetrical shape and they are not easily cut into the desired shape without damaging the structure or causing low yield. One can optionally cut a support into the desired shape first and then apply additional layers, but at the sacrifice of the economy of scale. Further, coating uniform layers and photopatterning is often not amenable to non-symmetrically shaped articles.

Thus, a need exists for an improved method for patterning multilayer structures. In particular, a method of patterning structures is needed that is capable of providing articles having shapes other than simple squares or parallelograms, with high precision and large throughput, but without the need for laser or mechanical dicing.

SUMMARY

In accordance with the present disclosure, a method of making a structure having a patterned base layer comprises: providing a layer of a radiation-sensitive resin; exposing the layer of radiation-sensitive resin to patterned radiation to form a base layer precursor having a first pattern of exposed radiation-sensitive resin and a second pattern of unexposed radiation-sensitive resin; providing a layer of fluoropolymer in a third pattern over the base layer precursor to form a first intermediate structure; treating the first intermediate structure to form a second intermediate structure; and selectively removing either the first or second pattern of resin by contacting the second intermediate structure with a resin developing agent, thereby forming the patterned base layer.

In an embodiment, the present disclosure is capable of providing articles having shapes other than simple squares or parallelograms, with high precision and large throughput, but without the need for mechanical dicing.

BRIEF DESCRIPTION OF DRAWINGS

FIG. 2 is a cross-sectional view depicting a layer of radiation-sensitive resin according to an embodiment of the present disclosure;

FIG. 3 is a cross-sectional view depicting the formation of base layer precursor according to an embodiment of the present disclosure;

FIG. 4A-4C is a series of cross-sectional views depicting various stages in the formation of a first intermediate structure according to an embodiment of the present disclosure;

FIG. 9A-9C is a series of cross-sectional views depicting various stages in the formation of a patterned base layer structure according to another embodiment of the present disclosure;

FIG. 10 is a plan view of a carrier substrate having a release layer and two patterned base layer structures provided over the carrier substrate according to an embodiment of the present disclosure;

FIG. 11 is a cross-sectional view taken along cut line A-A drawn in FIG. 10;

FIG. 12A-12B is a series of cross-sectional views depicting various stages in the formation of a secondary substrate structure according to an embodiment of the present disclosure;

FIG. 16 is a cross-sectional view taken along cut line C-C drawn in FIG. 15;

FIG. 17 is a cross-sectional view of a shank portion tip according to an embodiment of the present disclosure that further includes a modifying material;

FIG. 18A-18B is a series of cross-sectional views depicting various stages in the formation of a patterned base layer structure according to an embodiment of the present disclosure that further includes a protective fluoropolymer layer;

FIG. 19A-19E is a series of cross-sectional views depicting various stages in the formation of a patterned base layer structure according to an embodiment of the present disclosure;

FIG. 21 is a plan view depicting different areas (quadrants) of a square silicon chip.

DETAILED DESCRIPTION

It is to be understood that the attached drawings are for purposes of illustrating the concepts of the disclosure and may not be to scale.

Figure 1:
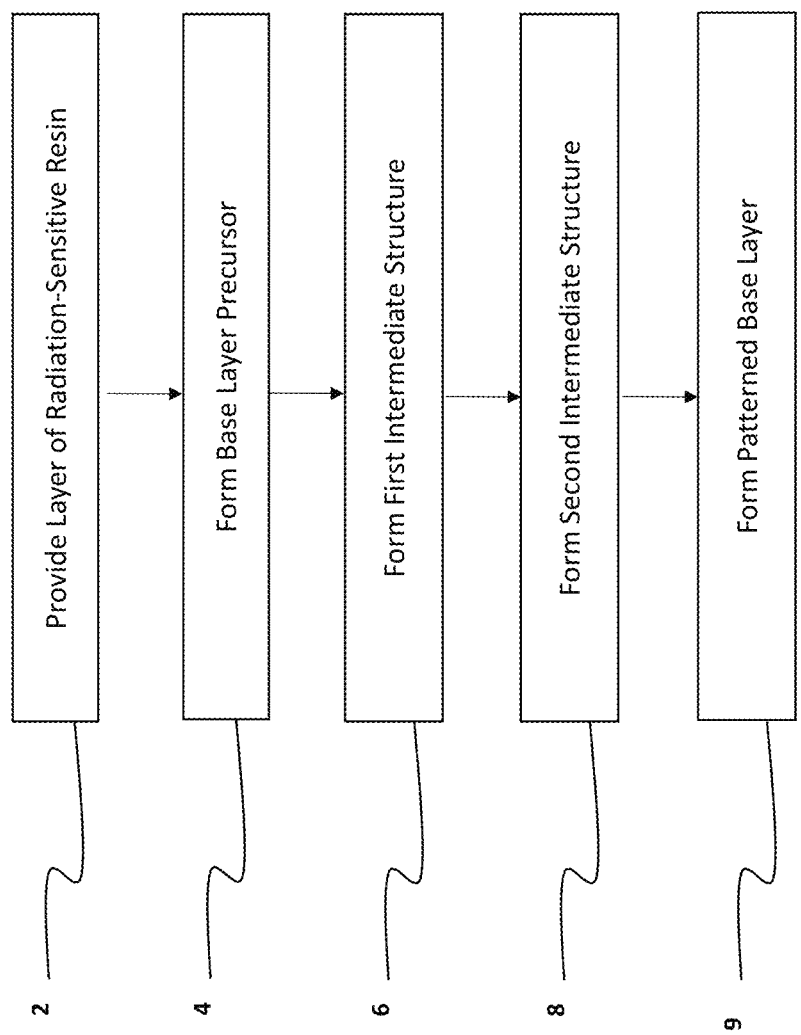
FIG. 1 is a flow chart depicting the steps in an embodiment of the present disclosure.

A flow diagram for an embodiment of the present disclosure is shown in FIG. 1, and includes the step 2 of providing a layer of radiation-sensitive resin, the step 4 of forming a base layer precursor, the step 6 of forming a first intermediate structure, the step 8 of forming a second intermediate structure, and the step 9 of forming a patterned base layer by contacting the second intermediate structure with a resin developing agent. Each step is discussed in more detail, below.

Turning to an embodiment shown in FIG. 2, a layer of radiation-sensitive resin 20 is provided over an optional carrier substrate 22 along with an optional intervening release layer 24. The layer of radiation-sensitive resin 20 may include any suitable material that can be selectively exposed to appropriate radiation to form exposed and unexposed areas having differential solubility in a resin developing agent. There is no particular limitation on the choice of radiation-sensitive material and such choice will depend largely upon its intended function in a patterned structure. The radiation-sensitive resin material can be primarily inorganic in nature (e.g., an imagable sol-gel), primarily organic (e.g., a photosensitive polymer) or a hybrid (e.g., a siloxane polymer). Some non-limiting examples of radiation-sensitive resins include epoxy-based photopolymers (such as SU8), phenol-formaldehyde photoresists (such as Novolac), photo polymerizable resins, photo-cross-linking resins (e.g., resins having vinyl groups such as styrenes, cinnamates and acrylates), and polymeric materials that can be modified as known in the art to impart photosensitivity (such as PDMS, silicones, polyimides, polystyrenes). The radiation-sensitive resin may optionally be bio-resorbable, e.g., based on a photosensitized polyethylene glycol (such as PEG diacrylate), polylactic acid, polyglycolic acid, polyvinylalcohol, polyacrylic acid, polycaprolactone, collagen, polyester-ether, a polyamino acid or a combination thereof. In an embodiment, the radiation-sensitive resin is selected to have low solubility in fluorinated solvents that may be used in subsequent steps. In an embodiment, the radiation-sensitive resin has a fluorine content by weight of less than 30%, preferably less than 15%. In an embodiment, the radiation-sensitive resin has a fluorine content of less than 1% by weight.

The layer of radiation-sensitive resin 20 may be provided as a preformed sheet or coated from as solution, e.g., by spin coating, curtain coating, doctor-blade coating, dip coating, ink jet coating, spray application or the like. The radiation-sensitive resin can be positive tone or negative tone. A positive tone resin is one where exposed areas are more soluble in the resin developing agent than unexposed areas. A negative tone resin is one where exposed areas are less soluble in the resin developing agent than unexposed areas. There is no particular limitation on the thickness of the layer of radiation-sensitive resin, other than it cannot be so thick that it will not properly image and that the final thickness will serve its intended purpose. In an embodiment, the layer of radiation-sensitive resin may have a thickness in a range of 0.5 to 1000 µm, or in another embodiment, a range of 10 to 100 µm, or in another embodiment, a range of 20 to 60 µm, or in another embodiment in a range of 0.5 to 10 µm.

The optional carrier substrate 22 is particularly useful when coating the radiation-sensitive resin from a solution. Such substrates are preferably flat and may be formed from sheets or wafers of glass, silicon, metal, ceramic, plastic or combinations thereof. The optional release layer 24 can be useful when one desires to separate a structure having a patterned base layer (see below) from a carrier substrate. The release layer may be a thin layer that simply lowers adhesion between layers (e.g., a layer of surfactant) or it may be a layer that has reasonable adhesion at first, but can be activated in some way, e.g., by thermal or light activation, to promote release when desired. Such materials are known in the art and some are used, e.g., as "light-to-heat conversion" layers or "transfer assist" layers in thermal and laser transfer from donor sheets to receivers. Some non-limiting examples of light-to-heat conversion layers can be found in WO 2008/010982, which is incorporated by reference herein.

The radiation used to expose the radiation-sensitive resin depends upon the resin. In an embodiment, the radiation may be relatively low energy such as infra-red, e.g., provided by a lamp, a laser or a heating element. In an embodiment, the radiation may be high energy such as X-ray or e-beam. In an embodiment, the radiation is visible or ultraviolet light. In a preferred embodiment, the radiation is in a wavelength range of 300 nm to 450 nm. Patterned visible or UV light may be provided across the layer of radiation-sensitive resin by, e.g., using a photomask in conjunction with a radiation source such as a mercury lamp, using a projection device that may optionally step and repeat across the resin, rastering a laser, scanning a series of LEDs or providing a digital matrix array of light-emitting elements in close proximity to the layer, or applying any other suitable method known in the art.

Turning to an embodiment shown in FIG. 3, a photomask 45 is provided between a radiation source that emits radiation 46 (e.g., "i-line" UV light at 365 nm) and the layer of radiation sensitive resin 20 (e.g., resin that is sensitive to 365 nm radiation), thereby forming a base layer precursor 40 having a first pattern 41 of exposed radiation-sensitive resin and a second pattern 42 of unexposed radiation-sensitive resin. In this embodiment, the radiation-sensitive resin is negative tone. For example, the patterned radiation causes cross-linking or polymerization in the first pattern of exposed radiation-sensitive resin making it less soluble in the resin developing agent. In some embodiments, the base layer precursor may need a secondary activation step such as a baking step, commonly referred to as a "post exposure bake" or "PEB". When that is the case, the PEB may be performed before other process steps, but in another embodiment, it may be done later in the process (but before contact with a resin developing agent). A feature of the present disclosure is that the base layer precursor undergoes further processing steps (patterning steps in particular, as detailed below) prior to contact with a resin developing agent, whereas in the prior art, a photosensitive resin is normally exposed and developed in sequence without any significant intervening process steps. Thus, the further processing steps are performed over a base layer precursor that is relatively flat, which may be advantageous. In an embodiment, thickness variations across the base layer precursor are within 50% of the average thickness, preferably less than 15% or more preferably less than 5%. In an embodiment, the thickness variations across a base layer precursor are less than 25 µm, preferably less than 8 µm and more preferably less than 2 µm. In an embodiment, the base layer precursor is selected to have low solubility in fluorinated solvents that may be used in subsequent steps.

A first intermediate structure is formed by providing a patterned layer of a fluoropolymer over the base layer precursors. By not first developing the base layer precursor, the surface is still generally flat, which enables many methods of applying or forming a patterned fluoropolymer. Some non-limiting examples include ink jet depositing a liquid containing a fluoropolymer, patterned thermal transfer of a dry fluoropolymer from a donor sheet, and flexographic printing of a liquid containing a fluoropolymer. In a preferred embodiment, the layer of patterned fluoropolymer is provided by coating a solution comprising a fluorinated solvent and a fluoropolymer and applying photolithographic methods, e.g., as disclosed in U.S. patent application publications 2011/0159252 and 2010/0289019, the entire contents of which are incorporated by reference. The generally flat base layer precursor simplifies coating and photolithography. In an embodiment, an intervening layer of another material may be provided between the patterned layer of fluoropolymer and the base layer precursor. Such other optional material layer and method of application should be selected so that is compatible with the base layer precursor (e.g., parylene). In a preferred embodiment, the fluoropolymer is provided in direct contact with the base layer precursor from a solution comprising a fluorinated solvent. It is often the case that either the exposed or unexposed areas of a radiation-sensitive resin are easily dissolved or otherwise altered by common organic solvents or aqueous media. This is the basis for how such photo-patternable resins work. Since the base layer precursor has both, this significantly limits the choice of layers one can apply directly on the base layer. It has been found that fluorinated solvents have been generally found to be "orthogonal" in solubility relative to both exposed and unexposed photosensitive resins, i.e., neither are easily dissolved into fluorinated solvents such as those described below. Thus, application of a patterned fluoropolymer using fluorinated solvents is particularly versatile.

FIGS. 4A-4C illustrate an embodiment for forming a first intermediate structure 67 using a photosensitive fluoropolymer. In FIG. 4A, a layer of photosensitive fluoropolymer 60 is formed by applying over the base layer precursor a composition comprising a photosensitive fluoropolymer material and a first fluorinated solvent, e.g., a hydrofluoroether solvent. The layer of photosensitive fluoropolymer 60 may include any suitable fluorinated material that can be selectively exposed to appropriate radiation to form exposed and unexposed areas having differential solubility in a fluoropolymer developing solution. The photosensitive fluoropolymer can be negative tone or positive tone, and as described below, there are numerous options for its chemical composition and image development. The photosensitive fluoropolymer 60 preferably has a different spectral sensitivity than the radiation-sensitive resin so that exposure of the photosensitive fluoropolymer does not cause unwanted exposure of the radiation-sensitive resin. In an alternative embodiment, the photosensitive fluoropolymer substantially absorbs enough radiation to prevent problematic exposure of the radiation-sensitive resin. In an alternative embodiment an intervening layer containing a light absorbing compound is provided between the base layer precursor and the photosensitive fluoropolymer. Alternatively, the photosensitive resin could be selected as one that requires, and is given, a PEB prior to application of the photosensitive fluoropolymer, and the selected fluoropolymer needs no PEB or PEB conditions that will not affect the underlying photosensitive resin. In the illustrated embodiment, the photosensitive fluoropolymer is negative tone and developable in a solution (a fluoropolymer developing agent) comprising one or more fluorinated solvents, e.g., a hydrofluoroether. Unless otherwise noted, the term "solution" is used broadly herein to mean any flowable material. Examples of "solutions" include, but are not limited to: single solvent liquids; homogeneous mixtures of a solvent with one or more other solvents, with one or more solutes, and combinations thereof; and heterogeneous or multi-phase mixtures such as emulsions, dispersions and the like.

Referring now to FIG. 4B, a photomask 62 is provided between radiation source emitting radiation 61 (e.g., "g-line" UV light at 436 nm) and the layer of photosensitive fluoropolymer (e.g., that is sensitive to 436 nm radiation), thereby forming an exposed layer of photosensitive fluoropolymer 63 having a pattern 64 of exposed photosensitive fluoropolymer and a pattern 65 of unexposed photosensitive fluoropolymer. In FIG. 4C, the exposed layer of photosensitive fluoropolymer 63 is then contacted with a photosensitive fluoropolymer developing agent, preferably having at least 50% by volume of a second fluorinated solvent (that may the same as or different from the first fluorinated solvent), to selectively remove unexposed areas of the photosensitive fluoropolymer thereby forming a layer of fluoropolymer in a third pattern 66 and first intermediate structure 67. Contacting can be accomplished by immersion into the developing agent or by coating the structure with the developing solution in some way, e.g., by spin coating or spray coating. The contacting can be performed multiple times if necessary.

The pattern 64 of exposed photosensitive fluoropolymer corresponds to the third pattern 66, but is not necessarily identical to it. Pattern 64 might be slightly larger or smaller than pattern 66 but will have generally the same shape. A difference may be caused, e.g., by non-uniformity at exposure edges, diffusion of activated photo-acid generator groups and development kinetics, in addition to many other potential sources. Although drawn as vertical, the sidewalls of the layer of fluoropolymer in a third pattern 66 may have some other shape after development. Rather than rectangular, its cross section could resemble a trapezoid, an inverted trapezoid (undercut), or some other shape, e.g., one having curved sidewalls.

In an alternative embodiment shown in FIGS. 5A-5D, photolithographic patterning is applied to a bilayer structure. In an embodiment shown in FIG. 5A, a layer of an initially non-patterned fluoropolymer 160 is applied over the base layer precursor, e.g., by coating from a solution or by dry film transfer from a donor sheet. In this embodiment, the fluoropolymer is soluble in one or more fluorinated solvents that do not interact significantly with the base layer precursor. Next, a layer of a photosensitive second polymer 161 (e.g., a photoresist) is provided over the non-patterned fluoropolymer 160 to form an unpatterned bilayer structure. The photosensitive second polymer 161 may, for example, be coated from an organic or aqueous solution in which the underlying non-patterned fluoropolymer is not soluble. The photosensitive second polymer 161 may be a photosensitive fluoropolymer coated from a fluorinated solvent that does not significantly dissolve or impact the underlying non-patterned fluoropolymer 160. The photosensitive second polymer 161 may alternatively be any conventional photoresist or photopolymer that can be coated and developed using aqueous or non-fluorinated organic solvents that do not deleteriously interact with the underlying fluoropolymer layer. The developed photosensitive second polymer should also have low solubility in fluorinated solvents used to pattern the underlying fluoropolymer layer (see below). In an embodiment, the photosensitive second polymer has a total fluorine content by weight of less than 30%, alternatively less than 15%. In an embodiment, the photosensitive second polymer has a total fluorine content of less that 1% by weight.

Figure 5A:
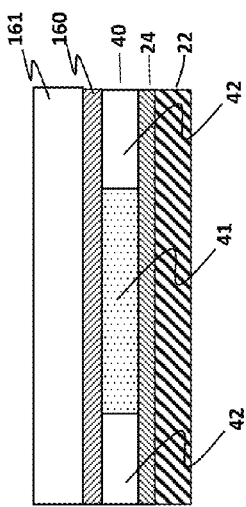
FIG. 5A-5D is a series of cross-sectional views depicting various stages in the formation of a first intermediate structure according to another embodiment of the present disclosure.
Figure 5C:
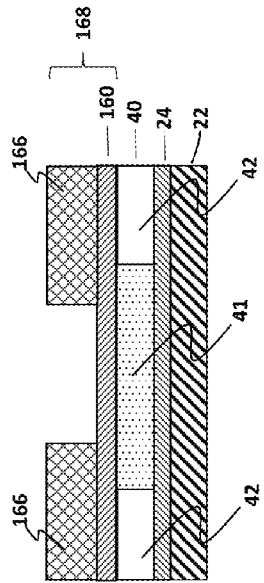
Figure 5B:
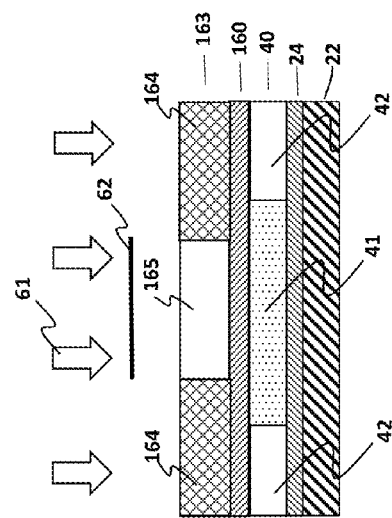

Referring now to FIG. 5B, a photomask 62 is provided between radiation source emitting radiation 61 (e.g., "g-line" UV light at 436 nm) and the layer of photosensitive second polymer (e.g., that is sensitive to 436 nm radiation), thereby forming an exposed layer of photosensitive second polymer 163 having a pattern 164 of exposed photosensitive second polymer and a pattern 165 of unexposed photosensitive second polymer. In FIG. 5C, the exposed layer of photosensitive second polymer 163 is then contacted with a second polymer developing agent to selectively remove unexposed areas of the photosensitive second polymer thereby forming a partially patterned bilayer structure 168 including a patterned layer 166 of second polymer corresponding to a third pattern provided over the non-patterned fluoropolymer layer 160. The non-patterned fluoropolymer 160 is not highly soluble in the second polymer developing agent and is not removed at this point. In an alternative embodiment, the patterned layer 166 of second polymer may be formed by printing.

Figure 5D:
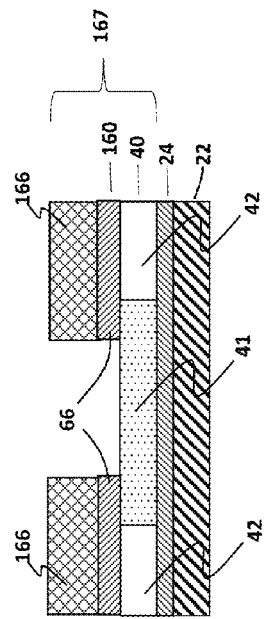

The partially patterned bilayer structure 168 is contacted with a fluorinated solvent in which the fluoropolymer has some solubility, but not the second polymer. As shown in FIG. 5D, this results in selective removal of the fluoropolymer in areas not covered by the second polymer, thereby forming a layer of fluoropolymer in a third pattern 66 and first intermediate structure 167. It should be noted that the solubility of the fluoropolymer in the fluorinated solvent may lead to some harmless undercutting (not shown), but this can be controlled through selection of time, temperature, choice of fluorinated solvents, agitation and the like. In some embodiments, the undercutting is desirable. If the contacting with the fluorinated solvent is done under conditions too aggressive, this may result in lift-off of the second polymer. This is not desired at this point, but may be desirable later on if patterning additional material layers.

The first intermediate structure is next treated to form a second intermediate structure. Herein, the term "treated" means that the first intermediate structure is acted upon by at least two subsequent process steps, not including any optional heating steps. These process steps can be chemical or physical in nature. For example, the treatment may include deposition of one or more additional material layers in a pattern. Alternatively, or in combination, the treatment may involve etching or modifying the surface of a material layer not covered by the third pattern of fluoropolymer, e.g., the base layer precursor or an intervening layer between the fluoropolymer and the third pattern. The treatment may involve the formation of a multilayer structure over the base layer precursor, which might involve many steps more than just two.

Figure 6A:
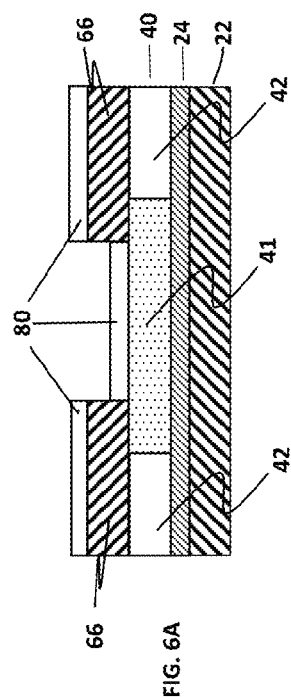
FIG. 6A-6B is a series of cross-sectional views depicting various stages in the formation of a second intermediate structure according to an embodiment of the present disclosure.
Figure 6B:
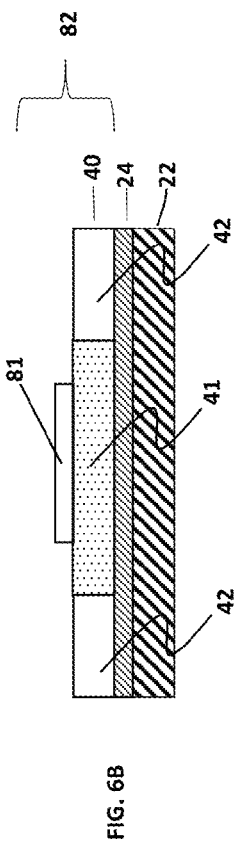

FIGS. 6A and 6B illustrate an embodiment wherein the treatment forms a patterned layer. In FIG. 6A, a material layer 80 is deposited over the first intermediate structure (from FIG. 4C) as a first step. The material can, for example, be coated in some way from a liquid or deposited from vacuum or vapor phase (sputtering, evaporation and the like). Multiple layers of different materials can optionally be deposited. There is no particular limitation on the choice of material, which will depend on the desired function. In the present embodiment, material layer 80 is a bilayer structure including an adhesion promoting material such as titanium and a thicker electrically conductive material such as gold. As shown in FIG. 6B, the structure is then contacted with a stripping solution capable of dissolving the third pattern of fluoropolymer, thereby lifting off the overlying material layer 80 and forming the second intermediate structure 82 having a patterned material layer 81. In the present embodiment, material layer 81 may be a conductive electrode.

The first pattern of exposed radiation-sensitive resin may have a first glass transition temperature (Tg) and the second pattern of unexposed radiation-sensitive resin may have a second Tg that is the same as or different from the first Tg. In an embodiment, the steps of forming the first and second intermediate structures do not subject the base layer precursor to temperatures that exceed the first Tg, and preferably, either the first Tg or the second Tg. In an embodiment, during the processing steps used to make the first and second intermediate structures, the temperature of the base layer precursor does not exceed 100° C., preferably 65° C. and more preferably 50° C. In some situations, it has been found that exposure to high temperatures may cause buckling or deformations in the base layer precursor. This is one reason that, if a secondary activation bake step (post exposure bake) is required on the base layer precursor as discussed above, this baking step is preferably done before further processing, as such dimensional changes in the base layer precursor will have less impact if they occur initially, before the formation of the first and second intermediate structures.

Figure 7:
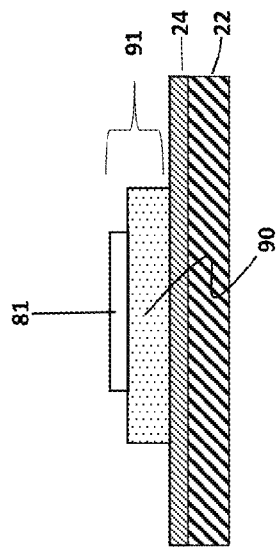
FIG. 7 is a cross-sectional view of a patterned base layer and a patterned base layer structure according to an embodiment of the present disclosure.

A patterned base layer is formed by contacting the second intermediate structure with a resin developing solution to remove either the first pattern of exposed radiation-sensitive resin or the second pattern of unexposed radiation-sensitive resin, depending on whether the resin material is positive or negative tone. In an embodiment illustrated in FIG. 7, the radiation-sensitive resin is negative tone and contact with the resin developing solution selectively removes second pattern 42 of unexposed radiation-sensitive resin, thereby forming patterned base layer 90. Contacting can be accomplished by immersion into the resin developing solution or by coating the structure with the resin developing solution in some way, e.g., by spin coating or spray coating. The contacting can be performed multiple times if necessary. Although drawn as vertical, the sidewalls of the patterned base layer 90 may have some other shape after development. Rather than rectangular, its cross section could resemble a trapezoid, an inverted trapezoid (undercut), or some other shape, e.g., one having curved sidewalls.

FIGS. 19A-19E illustrate another embodiment wherein treatment forms a patterned layer by using an etch method. In FIG. 19A a material layer 280 is deposited over the base layer precursor (from FIG. 4C). The material can, for example, be coated in some way from or as a liquid or deposited from vacuum or vapor phase (sputtering, evaporation and the like). If coated from a solvent or solution, it should be chosen not to have deleterious effects on the underlying base layer precursor. Multiple layers of different materials can optionally be deposited. Depending upon the optical properties of the material layer 280, it may optionally be deposited prior to exposure and optional post-exposure baking of the radiation sensitive resin. There is no particular limitation on the choice of material, which will depend on the desired function. In the present embodiment, material layer 280 is an organic semiconductor.

Referring to FIGS. 19A-19C, and in a manner analogous to that described with respect to FIGS. 4A-4C, a first intermediate structure 267 if formed by photopatterning a layer of photosensitive fluoropolymer 260 (provided over the material layer 280) using radiation source 261 and photomask 262 to form an exposed layer of photosensitive fluoropolymer 263 having a pattern 264 of exposed photosensitive fluoropolymer and a pattern 265 of unexposed photosensitive fluoropolymer. Following an optional post exposure bake, the exposed layer of photosensitive fluoropolymer 263 is contacted with a fluoropolymer developing agent to remove (in this embodiment) unexposed areas of photosensitive fluoropolymer thereby forming a layer of fluoropolymer in a third pattern 266 and the first intermediate structure 267.

FIG. 19D, the first intermediate structure 267 is treated by etching the material layer 280 that is not covered by the third pattern 266 of fluoropolymer, thereby forming patterned material layer 281 and second intermediate structure 282. Etching may be accomplished, for example by dry etching (e.g. by oxygen plasma) or wet etching (e.g., by using a solvent in which the material layer will dissolve or disperse into).

In FIG. 19E, a patterned base layer 290 and patterned base layer structure 291 are formed by development of the unexposed portions of the photosensitive resin. In the embodiment shown, the third pattern of fluoropolymer 266 has been removed, e.g., by contact with a fluorinated stripping agent. In an embodiment, the third pattern of fluoropolymer 266 is removed after development of the photosensitive resin. In an embodiment, etching of the material layer and development of the photosensitive resin is done in a common step prior to removal of the third pattern of fluoropolymer 266. In an alternative embodiment, the third pattern of fluoropolymer 266 is removed prior to development of the photosensitive resin. In another embodiment, the third pattern of fluoropolymer 266 is not removed at remains as part of the patterned base layer structure.

In an embodiment, the thickness of the patterned base layer is greater than the thickness of the patterned material layer. In an embodiment, the patterned base layer may have a Young's modulus of greater than 1 kPa, or when higher mechanical strength is required, greater than 0.01 GPa, or alternatively greater than 0.1 GPa, or alternatively greater than 1 GPa, depending on the physical requirements of its intended purpose. In an embodiment, the patterned base layer has a Tg of 100° C. or greater. For example, a patterned base layer made from an epoxy-cross linked photosensitive resin such as SU8 has been reported to have a Tg of about 200° C.

Figure 8:
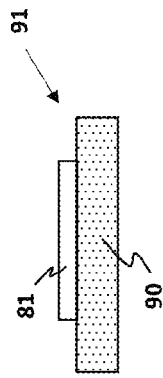
FIG. 8 is a cross-sectional view of a patterned base layer structure removed from an optional carrier substrate according to an embodiment of the present disclosure.

The patterned base layer 90 (or 290), along with layers and features formed over the patterned base layer, collectively, the patterned base layer structure 91 (or 291), may optionally be removed from the carrier substrate 22 as shown in FIG. 8. Non-limiting methods of such removal include physical peeling or pulling of the patterned base layer structure off of the carrier substrate, heating or cooling to cause differential expansion/contraction between patterned base layer structure and carrier substrate thereby causing separation, dissolving the release layer 24, or activating the release layer by light or heat to cause separation. A tool having an adhesive layer or gripping capability (mechanical, suction, magnetic or other means) may be applied to the top portion of the patterned base layer structure to aid in such removal. In an embodiment, the resin developing agent also dissolves the release layer 24 or otherwise causes release from the carrier substrate.

In an alternative embodiment shown in FIGS. 9A-9C, a second intermediate structure is first removed from the optional carrier substrate and then contacted with a resin developing agent. For example, a second intermediate structure 83 may be formed as described previously, but having a slightly different structure including areas of unexposed resin 42 directly beneath the patterned material layer 81 (FIG. 9A). Next, the second intermediate structure 83 is removed from the carrier substrate and release layer (FIG. 9B). Then, a second intermediate structure is contacted with a resin developing solution to form patterned base layer 92 and patterned base layer structure 93 (FIG. 9C). This alternative embodiment permits resin developing solution to reach unexposed resin areas that might not be otherwise accessible when the carrier substrate is still in place. The patterned material layer 81 may, for example, function as a membrane and have (from a top view, not shown) a circular structure supported at its edge by the patterned base layer.

There is no particular limitation on the shape of the patterned base layer. The shape may be symmetrical or asymmetrical, be simple or complex, have round or straight edges (or both) and the like. It depends upon the intended function of the base layer structure. The resolution of the shape is determined mainly by the sensitivity of radiation-sensitive resin material, the resolution of patterned radiation and the development kinetics when the base layer precursor is contacted with resin developing agent.

Multiple, separate base layer structures may be formed using the methods of the present disclosure. These individual base layer structures may be all identical in sizes and shapes, or some or all may be different. There is no particular limitation on the number of base layer structures that may be formed. In an embodiment, FIG. 10 shows a plan view of a carrier substrate having provided thereon a release layer 24 and two different patterned base layer structures formed over the release layer. A first patterned base layer structure 91a includes patterned base layer 90a and patterned material layer 81a. A second patterned base layer structure 91b includes patterned base layer 90b and patterned material layer 81b. The shapes and sizes of the two structures are different. This is further illustrated in FIG. 11 as a cross-sectional view taken along cut line A-A drawn in FIG. 10. In another embodiment, the patterned material layer 81a may comprise a different material than that of patterned material layer 81b. For example, the steps shown in FIGS. 4A-C and FIGS. 6A-B can be performed multiple times using different patterns and material layers. The first time can be used to pattern material layer 81a. The second time can be used to pattern material layer 81b. After both patterned material layers 81a and 81b have been formed (forming a second intermediate structure), the second intermediate structure can be contacted with a resin developing solution as previously described.

In an embodiment, one or more patterned base layer structures can be transferred to a second substrate. FIG. 12A illustrates an embodiment wherein both the first and second patterned base layer structures (91a and 91b, respectively) described in FIGS. 10 and 11 are transferred to secondary substrate 200. In this embodiment, the carrier substrate 22 acts as a donor sheet. There is no particular limitation on the secondary substrate 200 in this embodiment other than it be capable of receiving the patterned base layer structures. Secondary substrate 200 may optionally be a simple or complex multilayer structure, e.g., an electrical backplane. As shown in this embodiment, secondary substrate 200 may have an adhesion promoting layer 201 applied or patterned over the top to aid in the transfer of the first and second patterned base layer structures. An adhesion promoting layer may further serve another function, e.g., it can be a refractive index matching layer, an anisotropic conductor, a charge transport layer or the like. Upon application of pressure 210 and optionally heat or light (e.g. to activate release layer 24) or some other stimulus, adhesion between patterned base layer structures to the substrate or adhesion promoting layer exceeds the adhesion to the carrier substrate and the structures are transferred to the secondary substrate 200 as shown in FIG. 12B, thereby forming secondary substrate structure 220 wherein the patterned material layers face inwardly toward the secondary substrate.

In another embodiment, the patterned base layer structures are transferred to secondary substrate comprising a bioresorbable material for use in a bioelectronic or other biomedical device, e.g., an in vivo bioelectronic sensor.

In another embodiment, the one or more patterned base layer structures can be transferred to a second substrate by a "pick and place" operation. In pick and place, the patterned base layer structure is lifted (picked) off the carrier substrate by an intermediate mechanical assembly that can appropriately grip the structure, e.g., by physical coupling, through an adhesive layer, via magnetic means or the like. The intermediate mechanical assembly may optionally be a robotic device having an arm portion and a gripping portion. The intermediate mechanical assembly is subsequently positioned to allow placement of the patterned base layer structure onto a secondary substrate as desired. In this embodiment the patterned material layers face outwardly away from the secondary substrate.

In another embodiment, the one or more patterned base layer structures are released from a carrier substrate into an inert fluid, and the structures are transferred to a second substrate by fluidic self-assembly. In an embodiment, the second substrate has recessed features that uniquely match a particular base layer structure. For example, a secondary substrate may have a circular recess capable of selectively receiving a patterned base layer structure such as 91a and a rectangular recess capable of selectively receiving a patterned base layer structure such as 91b from a fluidic stream containing both types of patterned base layer structures.

The method according to the present disclosure can be used to fabricate devices such as electronic (including bioelectronic), optical, medical and mechanical (including MEMS) devices. In an embodiment, the patterned base layer structure includes an electronic or optical feature formed over the patterned base layer. For example, the feature may be provided by a patterned material layer. In some non-limiting examples, the feature may form a portion (or all) of a transistor, a capacitor, a light-emitting device, a touch screen, a photovoltaic device, a display device, a chemical sensor, a pressure sensor, a light sensor, a biosensor, a bio-stimulator, a bioelectronic ion pump, an organic electrochemical transistor, an electrochemical cell, a light guide, a lens, a reflector, a color filter, a microelectromechanical structure, a piezoelectric device or combinations thereof.

Figure 13:
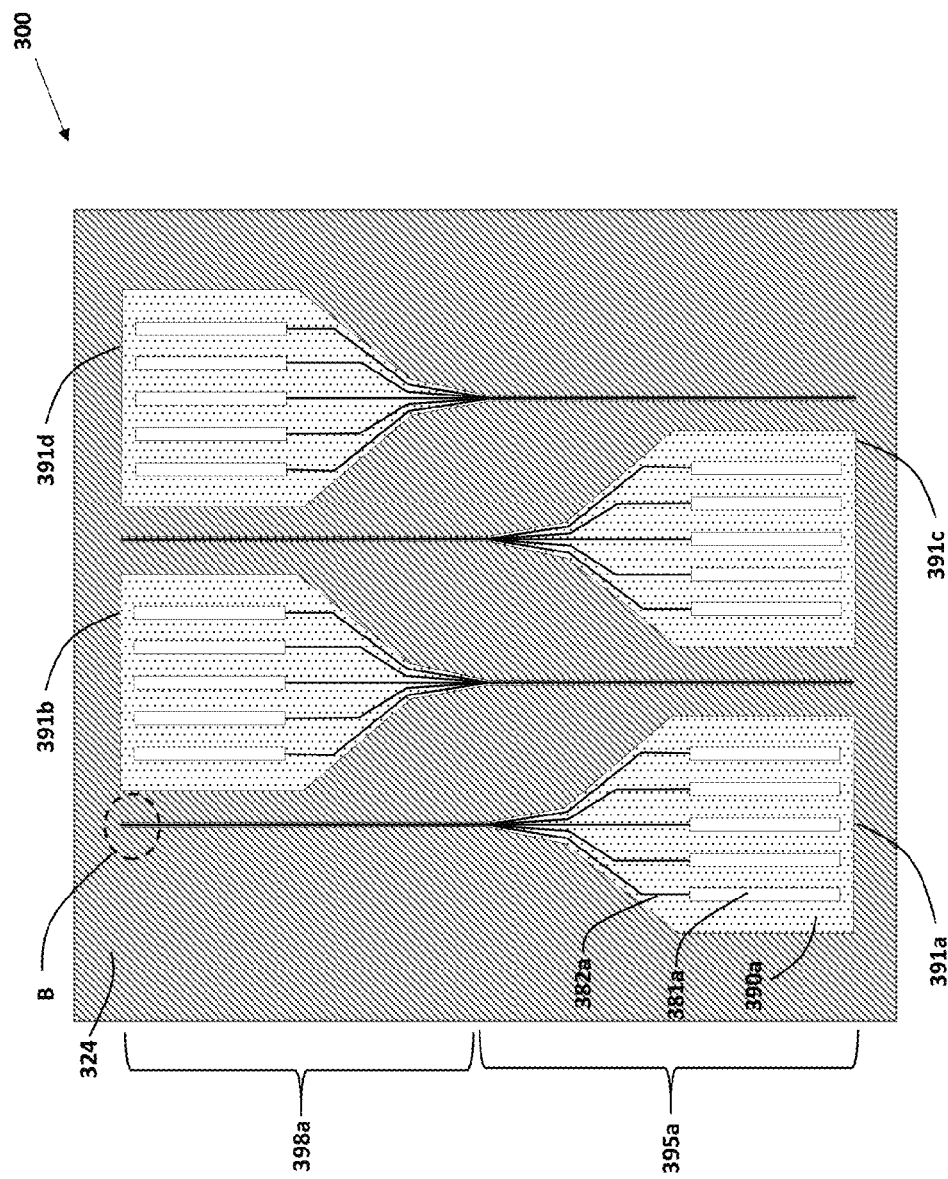
FIG. 13 is a plan view of a patterned base layer structure array according to an embodiment of the present disclosure.

As an example embodiment, FIG. 13 shows a plan view of a patterned base layer structure array 300. The array includes four patterned base layer structures, 391a, 391b, 391c, and 391d, provided over release layer 324 and a carrier substrate (not visible in this view). Each patterned base layer structure has a corresponding patterned base layer 390 (illustrated as 390a for base layer structure 391a) made, e.g., from SU8. Each of the patterned base layer structures in this embodiment forms a probe that may be used as bioelectronic device such as a biosensor or bio-stimulator. Each patterned base layer structure has an electrical contact portion 395 (illustrated as 395a for patterned base layer structure 391a) and a shank portion 398 (illustrated as 398a for patterned base layer structure 391a). The electrical contact portion 395 includes electrical contact pads 381 (illustrated as 381a for patterned base layer structure 391a) that provide connection to electronic driving circuitry (not shown). Conductive traces 382 (illustrated as 382a for patterned base layer structure 391a) provide electrical connection from the electrical contact pads 381 to electrode pads near the far tip of the shank. The electrode pads are very small in this embodiment and are not shown in FIG. 13. The shank portion 398 of the patterned base layer structure may optionally be designed to have sufficient mechanical strength to allow insertion into biological tissue, for example, the base layer structures in this embodiment are approximately 50 μm in thickness.

Figure 14:
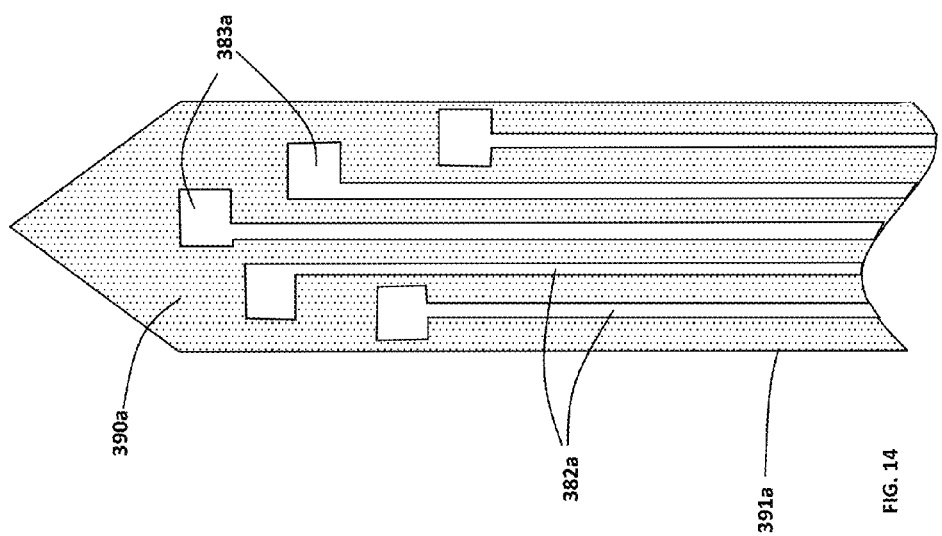
FIG. 14 is a plan view showing the tip of a shank portion of a patterned base layer structure according to an embodiment of the present disclosure.

The tip of shank portion 398 for patterned base layer structure 391a is highlighted by circle B in FIG. 13 and a magnified plan view is shown in FIG. 14 (excluding the release layer 24 for clarity). Five electrode pads 383a are provided near the pointed tip of the shank and each are individually electrically connected to conductive traces 382a that lead back to electrical contact pads 381a shown in FIG. 13.

The structures shown in FIGS. 13-14 can readily be produced using the methods disclosed above. Patterned contact pads 381, conductive traces 382 and electrode pads 383 are formed prior to contacting with a resin developing solution, e.g., using gold as the patterned material layer and a lift-off patterning process in conjunction with a negative tone, photosensitive fluoropolymer as discussed previously. In an embodiment, the photosensitive fluoropolymer used in the lift-off process is one having a carboxylic acid-forming precursor group or an alcohol-forming precursor group, or both, and development and stripping of the photosensitive fluoropolymer is done using two different fluorinated solvents.

The shank portion of the probe may optionally be inserted into biological tissue and each electrode pad may be electronically addressed to serve some function. In some non-limiting examples, an electrode pad may serve to inject charge into the tissue (bio-stimulator), it may serve to read out electrical impulses (bio-sensor), and it may be used to measure temperature. Each probe in this embodiment has five electrode pads, so each electrode pad may optionally serve different functions.

Figure 15:
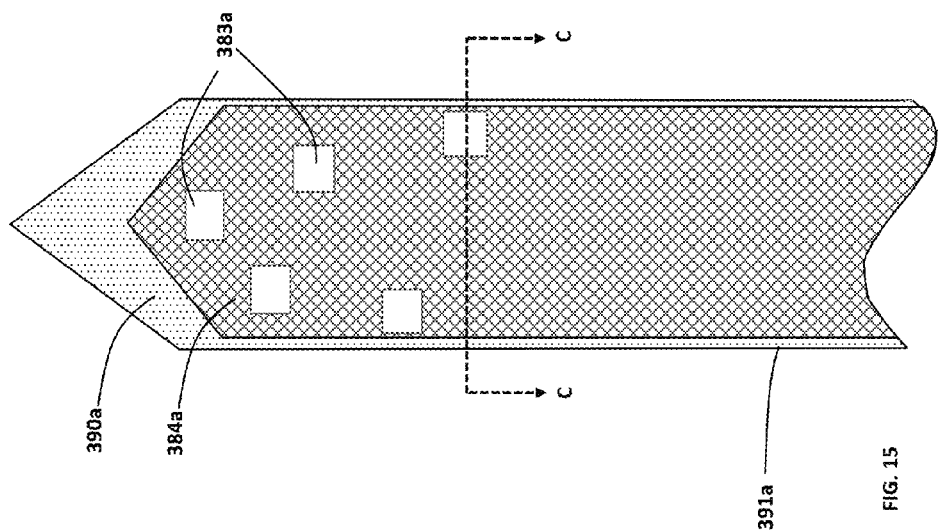
FIG. 15 is a plan view showing a shank portion tip according to another embodiment of the present disclosure.

In some cases, it may be advantageous to insulate the conductive traces so that only the electrode pads are in electrical contact to the desired target, e.g., biological tissue. FIG. 15 illustrates another embodiment similar to that shown in FIG. 14, but wherein a patterned second fluoropolymer 384a is provided over the conductive traces 382a and a portion of the patterned base layer 390a. In an embodiment, the patterned second fluoropolymer is provided by exposing and developing (using a fluorinated solvent) a photosensitive fluoropolymer that has cross-linking reactive groups. The patterned second fluoropolymer in the present embodiment is designed to stay in place as part of the probe device. FIG. 16 is a cross-sectional view taken along cut line C-C drawn in FIG. 15. The patterned second fluoropolymer layer is preferably formed prior to contacting with a resin developing solution, but it may optionally be formed afterwards. The electrode pads 383a revealed by the patterned second fluoropolymer 384a may have any suitable dimensions. Photolithographic patterning can enable very high resolution features having nearly any desired shape. In an embodiment, the revealed electrode features have an area in a range of 1 to 10,000 $\mu m^2$, or alternatively 25 to 2,500 $\mu m^2$.

One or more of the electrode pads may optionally be further modified. For example, an electrode modifying material, e.g., a conductive polymer such as PEDOT:PSS, may be provided over the electrode pad. An illustration is shown in FIG. 17 wherein a modifying material 385a is provided over electrode pad 383a from FIG. 16. In an embodiment, photolithographic patterning techniques mentioned earlier, e.g., etching or lift-off using the fluoropolymer, may be used to modify the electrode pad with a modifying material. Alternatively, a modifying material may be ink jetted over the electrode pad and into the well formed by the patterned second fluoropolymer. Since the electrode pads are addressable, a modifying material may be provided by electrochemical methods, e.g., by electroplating, electropolymerization, electrophoretic deposition, anodization of the electrode pad surface or the like. Alternatively, the electrode pad may be made of a material that selectively binds another chemical to form a modifying material layer. For example, a gold electrode pad can bind thiol-containing compounds to form a self-assembled monolayer of modifying material. Depending on compatibility of the modifying material, its application may be done before or after contacting with a resin developing solution. In an embodiment, the patterning of modifying material 385a is done prior to forming the patterned second fluoropolymer 384a, and the patterned second fluoropolymer may optionally extend over the top edges of modifying material 385a.

In an embodiment, the modifying material 385a is a conductive polymer such as PEDOT:PSS and forms part of an organic electrochemical transistor or a microelectrode array.

In some embodiments, a patterned material layer provided over the base layer precursor might not be readily compatible with the resin developing solution. When that is the case, a patterned protective fluoropolymer layer may be provided over the sensitive material. For example, although gold may be compatible with a resin developing solution, an electrode modifying material such as PEDOT:PSS might not be. An embodiment is shown in FIGS. 18A and 18B. Turning first to FIG. 18A, a structure like the one from FIG. 17 is provided, but shown having a base layer precursor 340 intact (comprising first pattern of exposed radiation-sensitive resin 341a and second pattern of unexposed radiation-sensitive resin 342), i.e., prior to contact with a resin developing agent. FIG. 18A further includes a patterned protective fluoropolymer layer 386a applied over modifying material 385a and a portion of patterned second fluoropolymer 384a. The protective fluoropolymer layer 386a protects the modifying material from the resin developing solution and FIG. 18B illustrates the structure after contact with the resin developing solution. The protective fluoropolymer may be applied and patterned using methods described earlier when forming the third pattern of fluoropolymer. In an embodiment, the protective fluoropolymer layer is formed from a photosensitive fluoropolymer. The protective fluoropolymer layer 386a may later be removed, e.g., by stripping with a fluorinated solvent (not shown in the figure) after formation of the patterned base layer.

Figure 20B:
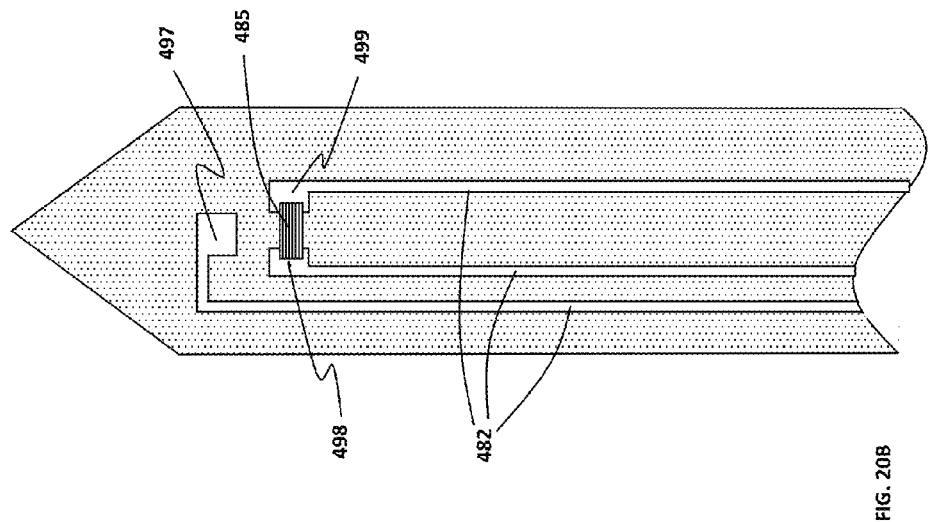
FIG. 20A-20B are plan views showing a OECT device provided on a shank portion tip according to an embodiment of the present disclosure.
Figure 20A:
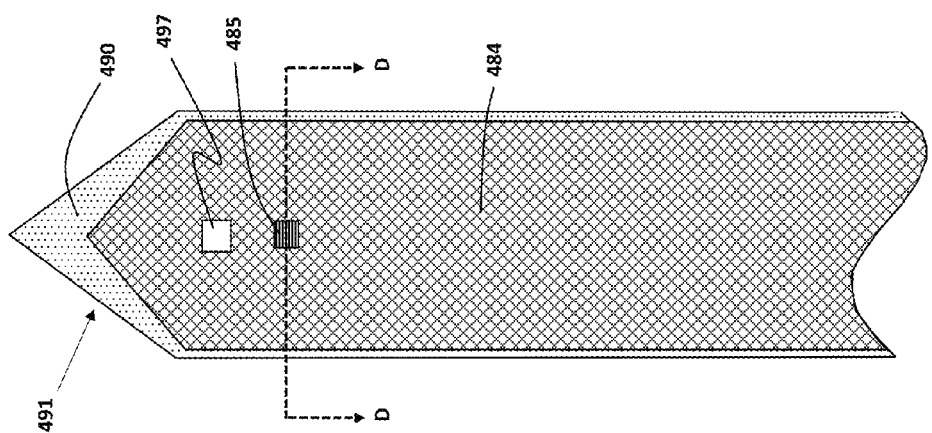
Figure 20C:
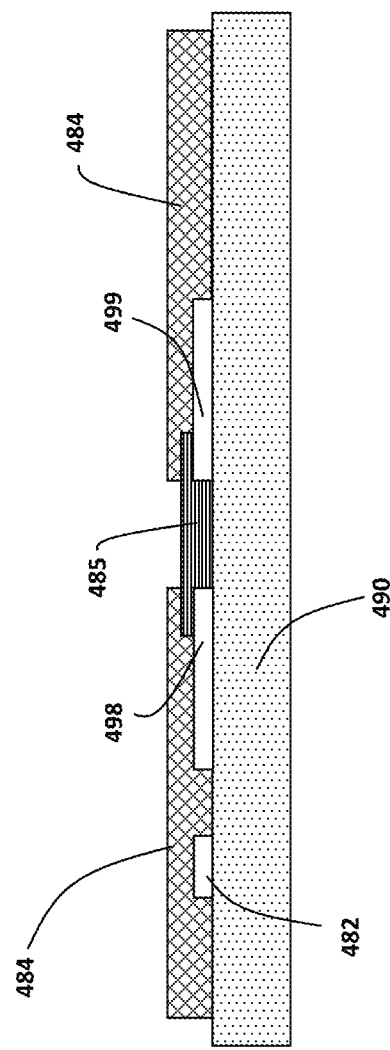
FIG. 20C is a cross-sectional view taken along cut line D-D drawn in FIG. 20A.

Methods of the present disclosure can be used to readily fabricate an organic electrochemical transistor (OECT) bioelectronic device, an embodiment of which is shown in FIGS. 20A, 20B and 20C. In FIG. 20A, there is shown a magnified view of a shank tip portion of a patterned base layer structure 491 that is similar in shape to the patterned base layer structures of FIG. 13, but the patterned base layer structure could instead have practically any shape. FIG. 20A shows a patterned base layer 490, an insulating patterned fluoropolymer 484, gate electrode 497, and patterned PEDOT:PSS 485 as the channel material. FIG. 20B is the same as FIG. 20A except with the patterned fluoropolymer 484 removed to illustrate the underlying drain electrode 498, source electrode 499 and conductive traces 482 connecting these electrodes back to an electrical contact portion (as described previously for related embodiments). FIG. 20C is a cross-sectional view of the device taken along cut line D-D drawn in FIG. 20A.

The patterned PEDOT:PSS is provided over a portion of the source and drain electrodes to make electrical contact, and over the patterned base layer in a portion extending between the source and drain electrodes. OECT devices are typically immersed in fluid media or biological tissue. The patterned fluoropolymer ensures that the source electrode, drain electrode and conductive traces are not in direct contact with the fluid or tissue. In the present embodiment, the fluoropolymer also covers an edge portion of the PEDOT:PSS. This can be advantageous in some embodiments (e.g., it may reduce the chances for delamination of the PEDOT:PSS during use), but it is not strictly necessary for the fluoropolymer to cover the PEDOT:PSS edge area. The gate electrode is separate from the source and drain electrodes and should also not be in direct contact with the patterned PEDOT:PSS. The gate electrode may have its own, separate PEDOT layer or some other modifying material provided over it. The gate electrode may also comprise different conductive material than the drain and source electrodes.

Methods described above can be used to fabricate the shown OECT. In a preferred embodiment when the device is intended for biological tissue use, the patterned base layer is formed from a photo cross-linking resin having a thickness of 10 to 100 µm. The conductive traces and electrodes are patterned by using a lift-off method utilizing a patterned fluoropolymer layer as described previously. In an embodiment, at least a portion of the conductive traces or one or more of the electrodes include a noble metal such as gold, platinum or silver, and may optionally include an adhesion layer such as titanium or chromium. Alternatively, the conductive traces or one or more electrodes may comprise a substantially transparent conductor such as ITO, graphene, or metal nanowires. The patterned PEDOT:PSS is preferably provided by first uniformly coating a PEDOT:PSS solution over a substructure having a base layer precursor, the conductive traces and electrodes, followed by applying an etch mask (e.g., a patterned fluoropolymer), etching the PEDOT and then removing the etch mask. This method permits uniform and predictable PEDOT:PSS film thickness which is very important for device performance, especially when preparing multiple OECT devices (over a single patterned base layer or over multiple patterned base layers). Over this structure, a photosensitive fluoropolymer can be applied and patterned to substantially cover the conductive traces, and the source and drain electrodes, but leaving open at least a portion of the gate electrode and the PEDOT:PSS channel. In a preferred embodiment, the photosensitive fluoropolymer is a cross-linking type of fluoropolymer. In an embodiment, the PEDOT:PSS channel covers an area (in a plan view such as FIG. 20A) in a range of about 10 µm$^2$ to about 500 µm$^2$. In an alternative embodiment, the gate electrode is not provided coplanar with the source and drain and may optionally be provided separately from the patterned base layer structure entirely (e.g. as a separate Ag or Ag/AgCl electrode). In an embodiment, the patterned base layer includes a plurality of independently addressable source and drain electrodes and corresponding patterned conductive polymers to form a plurality of OECTs. The patterned base layer may further include other devices in addition to the OECTs.

Examples of high-performance OECT devices are disclosed in Nature Communications 4, Article number 2133, Jul. 12, 2013, the contents of which are incorporated herein by reference. However, the methods disclosed in the Nature Communications article for making such OECT devices are not amenable to mass production (e.g., physically peeling off structures) and may need to be further modified to prepare effective in vivo devices. The methods of the present disclosure can be used to form uniform arrays of OECT devices (or other devices) having fine dimensions, nearly any shape, and on a large scale.

As mentioned above, certain processing steps of the present disclosure may include the use of a fluorinated solvent. When fluorinated solvents are used, they may be used in some embodiments as mixtures or solutions with non-fluorinated materials, but typically such mixtures include at least 50% by volume of a fluorinated solvent, preferably at least 90% by volume. Depending on the particular material set and solvation needs of the process, the fluorinated solvent may be selected from a broad range of materials such as chlorofluorocarbons (CFCs), hydrochlorofluorocarbons (HCFCs), hydrofluorocarbons (HFCs), perfluorocarbons (PFCs), hydrofluoroethers (HFEs), perfluoroethers, perfluoroamines, trifluoromethyl-substituted aromatic solvents, fluoroketones and the like.

Particularly useful fluorinated solvents include those that are perfluorinated or highly fluorinated liquids at room temperature, which are immiscible with water and most (but not necessarily all) organic solvents. Among those solvents, hydrofluoroethers (HFEs) are well known to be highly environmentally friendly, "green" solvents. HFEs, including segregated HFEs, are preferred solvents because they are non-flammable, have zero ozone-depletion potential, lower global warming potential than PFCs and show very low toxicity to humans.

Examples of readily available HFEs and isomeric mixtures of HFEs include, but are not limited to, an isomeric mixture of methyl nonafluorobutyl ether and methyl nonafluoroisobutyl ether (HFE-7100), an isomeric mixture of ethyl nonafluorobutyl ether and ethyl nonafluoroisobutyl ether (HFE-7200 aka Novec™ 7200), 3-ethoxy-1,1,1,2,3,4,4,5,5,6,6,6-dodecafluoro-2-trifluoromethyl-hexane (HFE-7500 aka Novec™ 7500), 1,1,1,2,3,3-hexafluoro-4-(1,1,2,3,3,3,-hexafluoropropoxy)-pentane (HFE-7600 aka Novec™ 7600), 1-methoxy-heptafluoropropane (HFE-7000), 1,1,1,2,2,3,4,5,5,5-decafluoro-3-methoxy-4-trifluoromethylpentane (HFE-7300 aka Novec™ 7300), 1,3-(1,1,2,2-tetrafluoroethoxy)benzene (HFE-978m), 1,2-(1,1,2,2-tetrafluoroethoxy)ethane (HFE-578E), 1,1,2,2-tetrafluoroethyl-1H,1H,5H-octafluoropentyl ether (HFE-6512), 1,1,2,2-tetrafluoroethyl-2,2,2-trifluoroethyl ether (HFE-347E), 1,1,2,2-tetrafluoroethyl-2,2,3,3-tetrafluoropropyl ether (HFE-458E), 2,3,3,4,4-pentafluorotetrahydro-5-methoxy-2,5-bis[1,2,2,2-tetrafluoro-1-(trifluoromethyl)ethyl]-furan (HFE-7700 aka Novec™ 7700) and 1,1,1,2,2,3,3,4,4,5,5,6,6-tridecafluorooctane-propyl ether (TE6O-C3).

Mixtures of fluorinated solvents may optionally be used, e.g., as disclosed in U.S. patent application Ser. Nos. 14/260,666 and 14/260,705, the entire contents of which are incorporated by reference herein.

The term "fluoropolymer" herein includes not only high molecular weight, long chain fluorinated materials, but also lower molecular weight oligomers, macrocyclic compounds such as fluorinated calixarene derivatives and other highly fluorinated hydrocarbons having at least 15 carbon atoms. In an embodiment, the molecular weight of the fluoropolymer is at least 750. In an embodiment, the fluoropolymer is soluble in one or more fluorinated solvents. Fluoropolymers preferably have a total fluorine content by weight in a range of 15% to 75%, or alternatively 30% to 75%, or alternatively 30% to 55%.

When the fluoropolymer is provided as a layer that is not inherently photosensitive (not directly photopatternable, such as described in FIG. 5), the fluorine content by weight is preferably in a range of 40% to 75%. Some non-limiting coatable examples of such polymers include Teflon AF (copolymer of tetrafluoroethylene with 2,2'-bis(trifluoromethyl)-4,5-difluoro-1,3-dioxole) and Cytop (a cyclic polymer formed from $F_2C=CFCF_2OCF=CF_2$). In an embodiment, the non-inherently photosensitive fluoropolymer is a copolymer comprising a fluorine-containing group (see below for examples) and a non-photosensitive functional group. The non-photosensitive functional group may improve film adhesion, improve coatability, adjust dissolution rate, absorb light, improve etch resistance and the like. In an embodiment, the non-photosensitive functional group is a non-fluorine-containing aromatic or aliphatic hydrocarbon that may optionally be substituted, for example, with oxygen-containing groups such as ethers, alcohols, esters, and carboxylic acids.

Photosensitive fluoropolymers can be provided, e.g., by coating a photosensitive fluoropolymer composition (also referred to herein as a fluorinated photopolymer composition) that includes a fluorinated solvent, a fluorinated photopolymer material, and optionally additional materials such as sensitizing dyes, photo-acid generator compounds, stabilizers, and the like. In an embodiment, the fluorinated photopolymer material includes a copolymer comprising at least two distinct repeating units, including a first repeating unit having a fluorine-containing group and a second repeating unit having a solubility-altering reactive group. In an embodiment using a fluorinated photopolymer that is a copolymer, the copolymer has a total fluorine content of at least 10%, preferably at least 15%. In an embodiment, the total fluorine content is in a range of 15% to 60%, alternatively 30 to 60%, or alternatively 35 to 55%. The copolymer is suitably a random copolymer, but other copolymer types may be used, e.g., block copolymers, alternating copolymers, and periodic copolymers. The term "repeating unit" herein is used broadly herein and simply means that there is more than one unit. The term is not intended to convey that there is necessarily any particular order or structure with respect to the other repeating units unless specified otherwise. When a repeating unit represents a low mole % of the combined repeating units, there may be only one such unit on a polymer chain. The copolymer may be optionally blended with one or more other polymers, preferably other fluorine-containing polymers. The fluoropolymer may optionally be branched, which may in certain embodiments enable lower fluorine content, faster development and stripping rates, or incorporation of groups that otherwise may have low solubility in a fluorinated polymer. Non-limiting examples of photosensitive fluoropolymer compositions are described in US Patent Publication 2011/0159252, U.S. patent application Ser. Nos. 14/113,408, 14/291,692, 14/335,476, US Provisional Patent Application Nos. 61/990,966, and 61/937,122, the contents of which are incorporated by reference.

In an embodiment, at least one of the specified repeat units is formed via a post-polymerization reaction. In this embodiment, an intermediate polymer (a precursor to the desired copolymer) is first prepared, said intermediate polymer comprising suitably reactive functional groups for forming one of more of the specified repeat units. For example, an intermediate polymer containing pendant carboxylic acid moieties can be reacted with a fluorinated alcohol compound in an esterification reaction to produce the specified fluorinated repeating unit. Similarly, a precursor polymer containing an alcohol can be reacted with a suitably derivatized glycidyl moiety to form an acid-catalyzed cross-linkable (epoxy-containing) repeating unit as the solubility-altering reactive group. In another example, a polymer containing a suitable leaving group such as primary halide can be reacted with an appropriate compound bearing a phenol moiety to form the desired repeat unit via an etherification reaction. In addition to simple condensation reactions such as esterification and amidation, and simple displacement reactions such as etherification, a variety of other covalent-bond forming reactions well-known to practitioners skilled in the art of organic synthesis can be used to form any of the specified repeat units. Examples include palladium-catalyzed coupling reactions, "click" reactions, addition to multiple bond reactions, Wittig reactions, reactions of acid halides with suitable nucleophiles, and the like.

In an alternative embodiment, the first and second repeating units of the copolymer are formed directly by polymerization of two (or more) appropriate monomers, rather than by attachment to an intermediate polymer. Although many of the embodiments below refer to polymerizable monomers, analogous structures and ranges are contemplated wherein one or more of the first and second repeating units are formed by attachment of the relevant group to an intermediate polymer as described above.

In an embodiment, the fluorinated photopolymer material includes a copolymer formed at least from a first monomer having a fluorine-containing group and a second monomer having a solubility-altering reactive group. Additional monomers may optionally be incorporated into the copolymer. The first monomer is one capable of being copolymerized with the second monomer and has at least one fluorine-containing group. In an embodiment, at least 70% of the fluorine content of the copolymer (by weight) is derived from the first monomer. In another embodiment, at least 85% of the fluorine content of the copolymer (by weight) is derived from the first monomer.

The first monomer includes a polymerizable group and a fluorine-containing group. Some non-limiting examples of useful polymerizable groups include acrylates (e.g. acrylate, methacrylate, cyanoacrylate and the like), acrylamides, vinylenes (e.g., styrenes), vinyl ethers and vinyl esters. The fluorine-containing group of the first monomer or the first repeating unit is preferably an alkyl or aryl group that may optionally be further substituted with chemical moieties other than fluorine, e.g., chlorine, a cyano group, or a substituted or unsubstituted alkyl, alkoxy, alkylthio, aryl, aryloxy, amino, alkanoate, benzoate, alkyl ester, aryl ester, alkanone, sulfonamide or monovalent heterocyclic group, or any other substituent that a skilled worker would readily contemplate that would not adversely affect the performance of the fluorinated photopolymer. Throughout this disclosure, unless otherwise specified, any use of the term alkyl includes straight-chain, branched and cyclo alkyls. In an embodiment, the first monomer does not contain protic or charged substituents, such as hydroxy, carboxylic acid, sulfonic acid or the like.

In an embodiment, the first monomer has a structure according to formula (1):

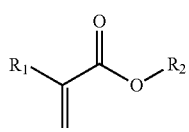

(1)

In formula (1), $R_1$ represents a hydrogen atom, a cyano group, a methyl group or an ethyl group. $R_2$ represents a fluorine-containing group, in particular, a substituted or unsubstituted alkyl group having at least 5 fluorine atoms, preferably at least 10 fluorine atoms. In an embodiment, the alkyl group is a cyclic or non-cyclic hydrofluorocarbon or hydrofluoroether having at least as many fluorine atoms as carbon atoms. In a preferred embodiment $R_2$ represents a perfluorinated alkyl or a 1H,1H,2H,2H-perfluorinated alkyl having at least 4 carbon atoms. An example of the latter is 1H,1H,2H,2H-perfluorooctyl methacrylate ("FOMA").

A combination of multiple first monomers or first repeating units having different fluorine-containing groups may be used. The total mole ratio of first monomers relative to all of the monomers of the copolymer may be in a range of 5 to 80%, or alternatively 10 to 70%, or alternatively 20 to 60%.

The second monomer is one capable of being copolymerized with the first monomer. The second monomer includes a polymerizable group and a solubility-altering reactive group. Some non-limiting examples of useful polymerizable groups include those described for the first monomer.

In an embodiment, the solubility-altering reactive group of the second monomer or second repeating unit is an acid-forming precursor group. Upon exposure to light, the acid-forming precursor group generates a polymer-bound acid group, e.g., a carboxylic or sulfonic acid. This can drastically change its solubility relative to the unexposed regions thereby allowing development of an image with the appropriate solvent. In an embodiment, the developing agent includes a fluorinated solvent that selectively dissolves unexposed areas. In an alternative embodiment, the developing agent includes a polar solvent that selectively dissolves the exposed areas. In an embodiment, a carboxylic acid-forming precursor is provided from a monomer in a weight percentage range of 4 to 40% relative to the copolymer, or alternatively in a weight percentage range of 10 to 30%.

One class of acid-forming precursor groups includes the non-chemically amplified type (i.e., non-acid catalyzed). An example of a second monomer with such a group is 2-nitrobenzyl methacrylate. The non-chemically amplified precursor group may directly absorb light to initiate de-protection of the acid-forming groups. Alternatively, a sensitizing dye may be added to the composition whereby the sensitizing dye absorbs light and forms an excited state capable of directly sensitizing or otherwise initiating the de-protection of acid-forming precursor groups. The sensitizing dye may be added as a small molecule or it may be attached or otherwise incorporated as part of the copolymer. Unlike chemically amplified formulations that rely on generation of an acid (see below), non-chemically amplified photopolymers may sometimes be preferred when a photopolymer is used in contact with an acid-sensitive or acid-containing material.

A second class of acid-forming precursor groups includes the chemically amplified type. This typically requires addition of a photo-acid generator (PAG) to the photopolymer composition, e.g., as a small molecule additive to the solution. The PAG may function by directly absorbing radiation (e.g. UV light) to cause decomposition of the PAG and release an acid. Alternatively, a sensitizing dye may be added to the composition whereby the sensitizing dye absorbs radiation and forms an excited state capable of reacting with a PAG to generate an acid. The sensitizing dye may be added as a small molecule, e.g., as disclosed in U.S. patent application Ser. No. 14/335,476, which is incorporated herein by reference. The sensitizing dye may be attached to or otherwise incorporated as part of the copolymer, e.g., as disclosed in U.S. patent application Ser. Nos. 14/291,692 and 14/291,767, which are incorporated herein by reference. In an embodiment, the sensitizing dye (either small molecule or attached) is fluorinated. In an embodiment, the sensitizing dye may be provided in a range of 0.5 to 10% by weight relative to the total copolymer weight. The photochemically generated acid catalyzes the de-protection of acid-labile protecting groups of the acid-forming precursor. In some embodiments, chemically amplified photopolymers can be particularly desirable since they enable the exposing step to be performed through the application of relatively low energy UV light exposure. This is advantageous since some active organic materials useful in applications to which the present disclosure pertains may decompose in the presence of UV light, and therefore, reduction of the energy during this step permits the photopolymer to be exposed without causing significant photolytic damage to underlying active organic layers. Also, reduced light exposure times improve the manufacturing throughput of the desired devices.

Examples of acid-forming precursor groups that yield a carboxylic acid include, but are not limited to: A) esters capable of forming, or rearranging to, a tertiary cation, e.g., t-butyl ester, t-amyl ester, 2-methyl-2-adamantyl ester, 1-ethylcyclopentyl ester, and 1-ethylcyclohexyl ester; B) esters of lactone, e.g., γ-butyrolactone-3-yl, γ-butyrolactone-2-yl, mevalonic lactone, 3-methyl-γ-butyrolactone-3-yl, 3-tetrahydrofuranyl, and 3-oxocyclohexyl; C) acetal esters, e.g., 2-tetrahydropyranyl, 2-tetrahydrofuranyl, and 2,3-propylenecarbonate-1-yl; D) beta-cyclic ketone esters, E) alpha-cyclic ether esters; and F) MEEMA (methoxy ethoxy ethyl methacrylate) and other esters which are easily hydrolyzable because of anchimeric assistance. In an embodiment, the second monomer comprises an acrylate-based polymerizable group and a tertiary alkyl ester acid-forming precursor group, e.g., t-butyl methacrylate ("TBMA") or 1-ethylcyclopentyl methacrylate ("ECPMA").

In an embodiment, the solubility-altering reactive group is an hydroxyl-forming precursor group (also referred to herein as an "alcohol-forming precursor group"). The hydroxyl-forming precursor includes an acid-labile protecting group and the photopolymer composition typically includes a PAG compound and operates as a "chemically amplified" type of system. Upon exposure to light, the PAG generates an acid (either directly or via a sensitizing dye as described above), which in turn, catalyzes the deprotection of the hydroxyl-forming precursor group, thereby forming a polymer-bound alcohol (hydroxyl group). This significantly changes its solubility relative to the unexposed regions thereby allowing development of an image with the appropriate solvent (typically fluorinated). In an embodiment, the developing agent includes a fluorinated solvent that selectively dissolves unexposed areas. In an alternative embodiment, the developing agent includes a polar solvent that selectively dissolves the exposed areas. In an embodiment, an hydroxyl-forming precursor is provided from a monomer in a weight percentage range of 4 to 40% relative to the copolymer.

In an embodiment, the hydroxyl-forming precursor has a structure according to formula (2):

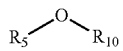

(2)

wherein $R_5$ is a carbon atom that forms part of the second repeating unit or second monomer, and $R_{10}$ is an acid-labile protecting group. Non-limiting examples of useful acid-labile protecting groups include those of formula (AL-1), acetal groups of the formula (AL-2), tertiary alkyl groups of the formula (AL-3) and silane groups of the formula (AL-4).

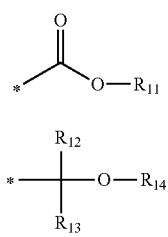

(AL-1)

(AL-2)

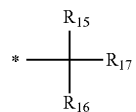

(AL-3)

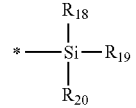

(AL-4)

In formula (AL-1), $R_{11}$ is a monovalent hydrocarbon group, typically a straight, branched or cyclic alkyl group, of 1 to 20 carbon atoms that may optionally be substituted with groups that a skilled worker would readily contemplate would not adversely affect the performance of the precursor. In an embodiment, $R_{11}$ may be a tertiary alkyl group. Some representative examples of formula (AL-1) include:

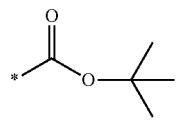

AL-1-1

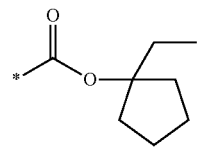

AL-1-2

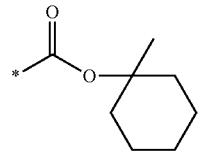

AL-1-3

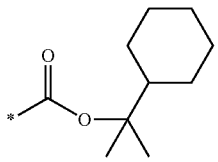

AL-1-4

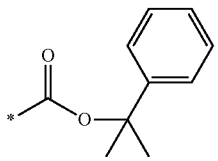

AL-1-5

In formula (AL-2), $R_{14}$ is a monovalent hydrocarbon group, typically a straight, branched or cyclic alkyl group, of 1 to 20 carbon atoms that may optionally be substituted. $R_{12}$ and $R_{13}$ are independently selected hydrogen or a monovalent hydrocarbon group, typically a straight, branched or cyclic alkyl group, of 1 to 20 carbon atoms that may optionally be substituted. Some representative examples of formula (AL-2) include:

AL-2-1

AL-2-2

AL-2-3

AL-2-4

AL-2-5

AL-2-6

AL-2-7

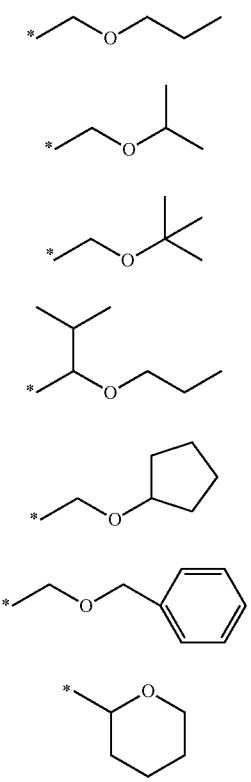

In formula (AL-3), $R_{15}$, $R_{16}$, and $R_{17}$ represent an independently selected a monovalent hydrocarbon group, typically a straight, branched or cyclic alkyl group, of 1 to 20 carbon atoms that may optionally be substituted. Some representative examples of formula (AL-3) include:

AL-3-1

AL-3-2

AL-3-3

AL-3-4

AL-3-5

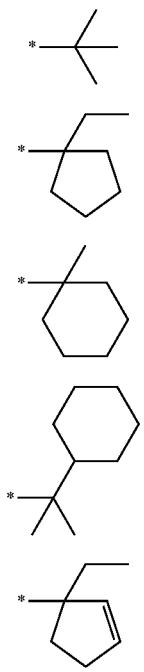

AL-3-6

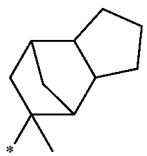

In formula (AL-4), $R_{18}$, $R_{19}$ and $R_{20}$ are independently selected hydrocarbon groups, typically a straight, branched or cyclic alkyl group, of 1 to 20 carbon atoms that may optionally be substituted.

The descriptions of the above acid-labile protecting groups for formulae (AL-2), (AL-3) and (AL-4) have been described in the context of hydroxyl-forming precursors. These same acid-labile protecting groups, when attached instead to a carboxylate group, may also be used to make some of the acid-forming precursor groups described earlier.

In an embodiment, the solubility-altering reactive group is a cross-linkable group, e.g., an acid-catalyzed cross-linkable group or a photo cross-linkable (non-acid catalyzed) group. Photo cross-linkable groups typically have at least one double bond so that when the group forms an excited state (either by direct absorption of light or by excited state transfer from a sensitizing dye), sets of double bonds from adjacent polymer chains crosslink. In an embodiment, the photo cross-linkable group (not catalyzed) comprises a cinnamate that may optionally further include fluorine-containing substituents, as described in U.S. Provisional Application No. 61/937,122, the contents of which are incorporated herein. Some non-limiting examples of polymerizable monomers including such cinnamates are shown below

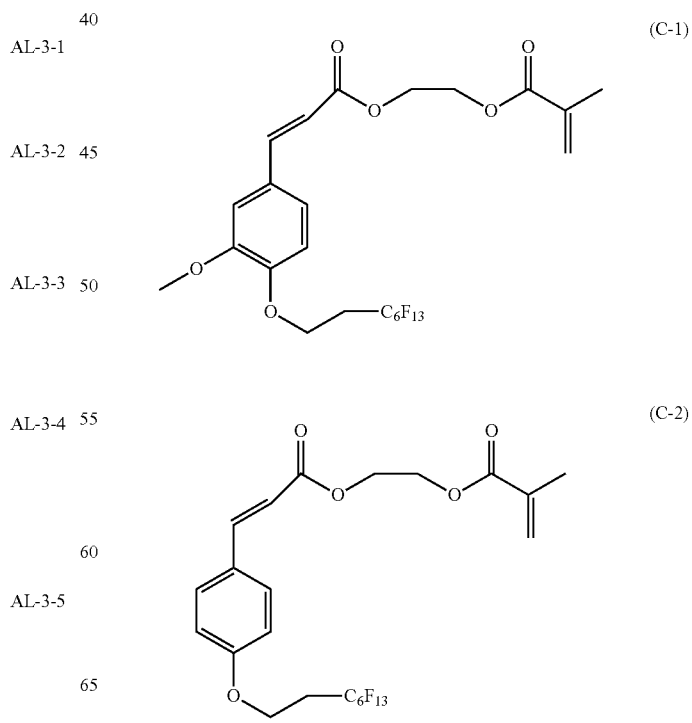

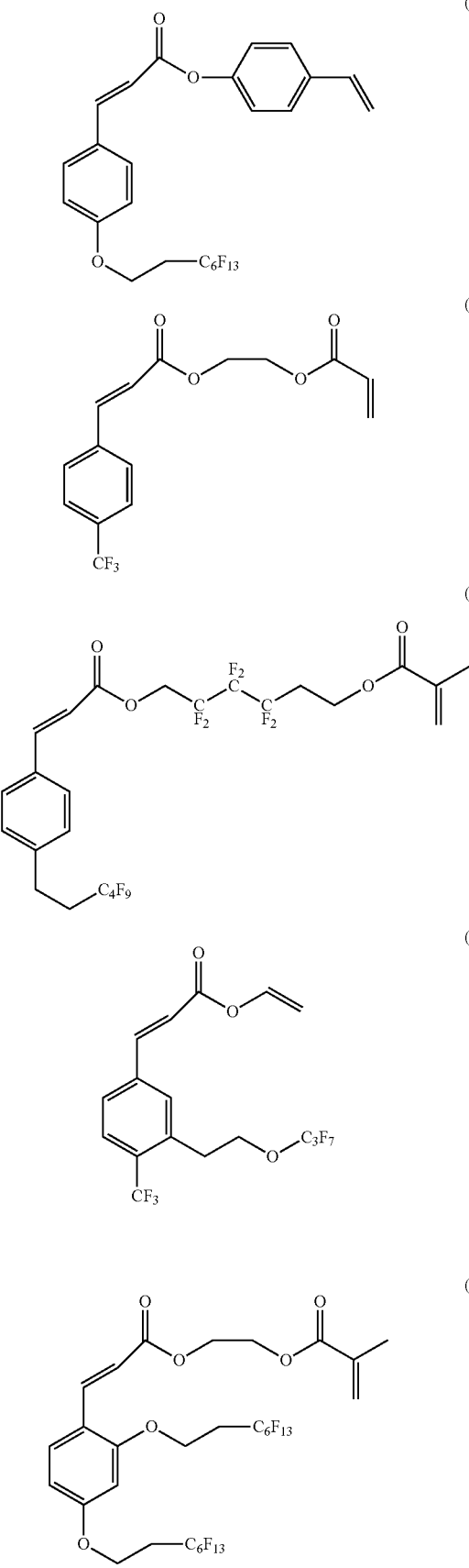

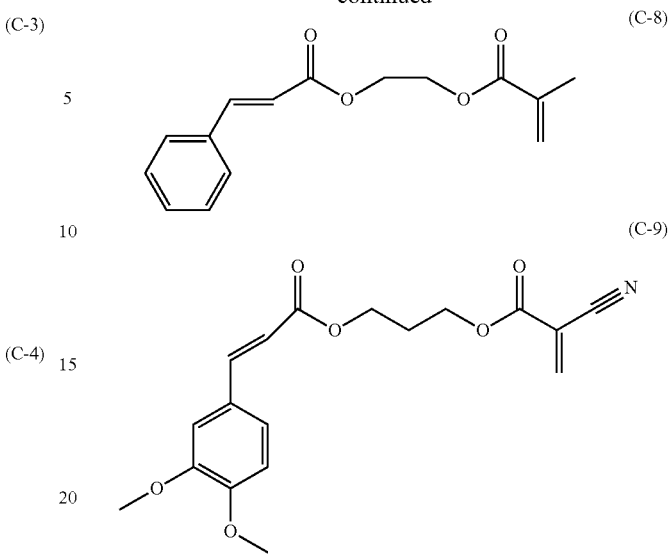

Compositions comprising such materials may optionally further include a sensitizing dye. Some non-limiting examples of useful sensitizing dyes for cinnamate cross-linking groups include diaryl ketones (e.g., benzophenones), arylalkyl ketones (e.g., acetophenones), diaryl butadienes, diaryl diketones (e.g. benzils), xanthones, thioxanthones, naphthalenes, anthracenes, benzanthrone, phenanthrenes, crysens, anthrones, 5-nitroacenapthene, 4-nitroaniline, 3-nitrofluorene, 4-nitromethylaniline, 4-nitrobiphenyl, picramide, 4-nitro-2,6-dichlorodimethylaniline, Michler's ketone, N-acyl-4-nitro-1-naphthylamine.

Examples of acid-catalyzed cross-linkable groups include, but are not limited to, cyclic ether groups and vinyloxy groups. In an embodiment, the cyclic ether is an epoxide or an oxetane. The photopolymer composition including an acid-catalyzed cross-linkable group typically includes a PAG compound and operates as a "chemically amplified" type of system in a manner described above. Upon exposure to light, the PAG generates an acid (either directly or via a sensitizing dye as described above), which in turn, catalyzes the cross-linking of the acid-catalyzed cross-linkable groups. This significantly changes its solubility relative to the unexposed regions thereby allowing development of an image with the appropriate fluorinated solvent. Usually, cross-linking reduces solubility. In an embodiment, the developing agent includes a fluorinated solvent that selectively dissolves unexposed areas. In an embodiment, a cross-linkable group is provided from a monomer in a weight percentage range of 4 to 40% relative to the copolymer.

Some non-limiting examples of some acid-catalyzed cross-linkable groups include the following wherein (*) refers to an attachment site to the polymer or the polymerizable group of a monomer:

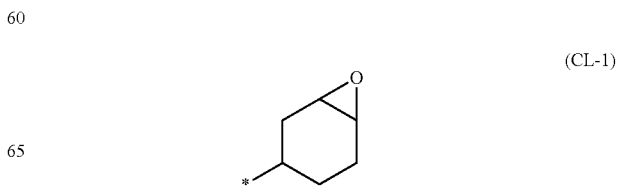

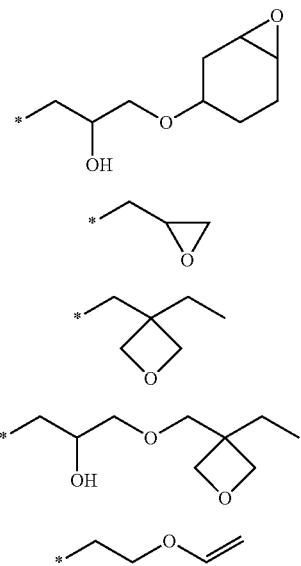

In an embodiment, the solubility-altering reactive groups are ones that, when the photopolymer composition or layer is exposed to light, undergo a bond-breaking reaction to form a material with higher solubility in fluorinated solvents. For example, the solubility-altering reactive groups could be cross-linked and the links are broken upon exposure to light thereby forming lower molecular weight materials. In this embodiment, a fluorinated solvent may be selected to selectively remove exposed areas, thereby acting as a positive photopolymer system.

A combination of multiple second monomers or second repeating units having different solubility-altering reactive groups may be used. For example, a fluorinated photopolymer may comprise both acid-forming and an alcohol-forming precursor groups.

The copolymer may optionally include additional repeating units having other functional groups or purposes. For example, the copolymer may optionally include a repeating unit that adjusts some photopolymer or film property (e.g., solubility, Tg, light absorption, sensitization efficiency, adhesion, surface wetting, etch resistance, dielectric constant, branching and the like).

Many useful PAG compounds exist that may be added to a photopolymer composition. In the presence of proper exposure and sensitization, this photo-acid generator will liberate an acid, which will react with the second monomer portion of the fluorinated photopolymer material to transform it into a less soluble form with respect to fluorinated solvents. The PAG needs to have some solubility in the coating solvent. The amount of PAG required depends upon the particular system, but generally, will be in a range of 0.1 to 6% by weight relative to the copolymer. In an embodiment, the amount of PAG is in a range of 0.1 to 2% relative to the copolymer. Fluorinated PAGs are generally preferred and non-ionic PAGs are particularly useful. Some useful examples of PAG compounds include 2-[2,2,3,3,4,4,5,5-octafluoro-1-(nonafluorobutylsulfonyloxyimino)-pentyl]-fluorene (ONPF) and 2-[2,2,3,3,4,4,4-heptafluoro-1-(nonafluorobutylsulfonyloxyimino)-butyl]-fluorene (HNBF). Other non-ionic PAGS include: norbornene-based non-ionic PAGs such as N-hydroxy-5-norbornene-2,3-dicarboximide perfluorooctanesulfonate, N-hydroxy-5-norbornene-2,3-dicarboximide perfluorobutanesulfonate, and N-hydroxy-5-norbornene-2,3-dicarboximide trifluoromethanesulfonate; and naphthalene-based non-ionic PAGs such as N-hydroxynaphthalimide perfluorooctanesulfonate, N-hydroxynaphthalimide perfluorobutanesulfonate and N-hydroxynaphthalimide trifluoromethanesulfonate. Suitable PAGs are not limited to those specifically mentioned above and some ionic PAGs can work, too. Combinations of two or more PAGs may be used as well.

REPRESENTATIVE EMBODIMENTS

Below are some non-limiting, representative embodiments of the present disclosure.

1. A method of making a structure having a patterned base layer, comprising the steps of:
providing a layer of a radiation-sensitive resin;
exposing the layer of radiation-sensitive resin to patterned radiation to form a base layer precursor having a first pattern of exposed radiation-sensitive resin and a second pattern of unexposed radiation-sensitive resin;
providing a layer of fluoropolymer in a third pattern over the base layer precursor to form a first intermediate structure;
treating the first intermediate structure to form a second intermediate structure; and
selectively removing either the first or second pattern of resin by contacting the second intermediate structure with a resin developing agent, thereby forming the patterned base layer.

2. The method according to embodiment 1 wherein the layer of radiation-sensitive resin is provided over a carrier substrate.

3. The method according to embodiment 1 or 2 wherein the structure includes at least one electronic or optical feature that is provided over the patterned base layer.

4. The method according to embodiment 3 wherein the electronic or optical feature forms at least a portion of a transistor, a capacitor, a light-emitting device, a touch screen, a photovoltaic device, a display device, a chemical sensor, a light sensor, a bio-sensor, a bio-stimulator, a bioelectronic ion pump, an electrochemical cell, an organic electrochemical transistor, a light guide, a lens, a reflector, a color filter, a piezo device, a MEMS device or combinations thereof.

5. The method according to any of embodiments 1-4 wherein the patterned base layer has a Young's modulus of 1 kPa or higher.

6. The method according to any of embodiments 1-5 wherein the patterned base layer has a Tg of 100° C. or higher.

7. The method according to embodiment 2 further including removal of the second intermediate structure or the patterned base layer from the carrier support.

8. The method according to embodiment 7 further comprising providing a release layer between the carrier support and the layer of radiation-sensitive resin, wherein the release layer promotes removal of the second intermediate structure or the patterned base layer.

9. The method according to any of embodiments 2-8 wherein the structure having a patterned base layer is one of a plurality of concurrently formed structures, each having a patterned base layer.

10. The method according to embodiment 9 wherein at least one of the plurality of structures has a patterned base layer in a first shape and at least one other of the plurality of structures has a patterned base layer in a second shape different from the first shape.

11. The method according to any of embodiments 7-10 further comprising transferring the structure to a secondary substrate.

12. The method according to any of embodiments 1-8 wherein the patterned base layer has an elongated shape and the structure has sufficient mechanical strength to allow insertion into biological tissue.

13. The method according to any of embodiments 1-12 wherein the patterned base layer has a thickness in a range of 10 to 100 μm.

14. The method according to any of embodiments 1-13 wherein the patterned radiation causes cross-linking or polymerization in the first pattern of exposed radiation-sensitive resin, whereby contact with the resin developing agent selectively removes the second pattern of unexposed radiation-sensitive resin.

15. The method according to embodiment 14 wherein the radiation-sensitive resin comprises an epoxy- or acrylate-based cross linkable group.

16. The method according to any of embodiments 1-15 wherein the third pattern of fluoropolymer is provided by:
   i) applying a composition comprising a photosensitive fluoropolymer material and a first fluorinated solvent to form a layer of photosensitive fluoropolymer;
   ii) exposing the photosensitive fluoropolymer to radiation in a pattern corresponding to the third pattern, thereby forming an exposed layer of photosensitive fluoropolymer; and
   iii) contacting the exposed layer of photosensitive fluoropolymer with a photosensitive fluoropolymer developing agent comprising at least 50% by volume of a second fluorinated solvent to selectively remove unexposed areas of the photosensitive fluoropolymer.

17. The method according to embodiment 16 wherein the photosensitive fluoropolymer material comprises a copolymer having at least two distinct repeating units, including a first repeating unit having a fluorine-containing group and a second repeating unit having a solubility-altering reactive group.

18. The method according to embodiment 17 wherein the solubility-altering reactive group is a carboxylic or sulfonic acid-forming precursor group, an alcohol-forming precursor group or a cross-linking group.

19. The method according to embodiments 16-18, wherein the first or second fluorinated solvent, or both, includes a hydrofluoroether.

20. The method according to any of embodiments 1-19 wherein the fluorine content of the fluoropolymer is in a range of 15-60% by weight.

21. The method according to any of embodiments 1-15 wherein the third pattern of fluoropolymer is provided by:
   a) applying a layer of non-patterned fluoropolymer over the base layer precursor, wherein the fluoropolymer is soluble in a fluorinated solvent;
   b) providing over the layer of non-patterned fluorinated polymer a layer of a second polymer in a pattern corresponding to the third pattern to form a partially patterned bilayer polymer structure, wherein the second polymer is substantially insoluble in the fluorinated solvent; and
   c) contacting the partially patterned bilayer polymer structure with the fluorinated solvent to selectively remove the fluoropolymer in areas not covered by the second polymer.

22. The method according to embodiment 21 wherein the second polymer is a photoresist having a total fluorine content by weight of less than 15% and the fluoropolymer has a total fluorine content by weight of greater than 40%.

23. The method according to embodiments 21 or 22 wherein the fluorinated solvent includes a hydrofluoroether, a hydrofluorocarbon or a perfluorinated compound.

24. The method according to any of embodiments 1-23 wherein the treating includes depositing a first material layer over the first intermediate structure.

25. The method according to embodiment 24 wherein the fluoropolymer is removed, thereby removing first material over the third pattern of fluoropolymer and forming a patterned first material layer in areas other than the third pattern.

26. The method according to embodiment 24 or 25 wherein the first material layer forms at least a portion of an electronic or optical feature.

27. The method according to embodiment 26 wherein the first material is a metal conductor.

28. The method according to embodiment 26 wherein the first material is an organic conductor, an organic semiconductor or an organic light-emitting material.

29. The method according to any of embodiments 1-28 further comprising providing a second material layer over the radiation sensitive resin and prior to providing the layer of fluoropolymer in a third pattern, and wherein the treating comprises etching the second material layer using the third pattern of fluoropolymer as an etch mask.

30. The method according to embodiment 29 wherein the second material is an organic conductor, an organic semiconductor or an organic light-emitting material.

31. The method according to embodiments 29 or 30 further comprising removal of the third pattern of fluoropolymer to form an uncovered patterned second material layer in areas corresponding to the third pattern.

32. The method according to any one of embodiments 1-31 wherein the first pattern of exposed radiation-sensitive resin has a first Tg and the second pattern of unexposed radiation-sensitive resin has a second Tg, and wherein the steps of forming the first and second intermediate structures do not subject the base layer precursor to temperatures that exceed either the first Tg or the second Tg.

33. An organic electrochemical transistor device comprising:
   a patterned base layer comprising a photochemically cross linked resin;
   a source electrode separated from a drain electrode provided over the patterned base layer;
   a patterned conductive polymer provided over at least a portion of the source and drain electrodes and over the patterned base layer in a portion extending between the source and drain electrodes; and
   an insulating patterned fluoropolymer layer provided over the source and drain electrodes and further includes an opening over the portion of conductive polymer extending between the source and drain electrodes.

34. The device of embodiment 33 further comprising a gate electrode provided over the patterned base layer but separate from the patterned conductive polymer.

35. The device of embodiment 33 or 34 further comprising conductive traces extending from the electrodes to an electrical contact portion of the patterned base layer, wherein the insulating patterned fluoropolymer layer covers the conductive traces in regions intended for immersion into a fluid or biological tissue sample.

36. The device according to any of embodiments 33-35 wherein patterned fluoropolymer layer is a photochemically cross-linked fluoropolymer.

37. The device according to any of embodiments 33-36 wherein the photochemically cross-linked resin has a thickness in a range of 10 to 100 μm.

38. The device according to any of embodiments 33-37 wherein the opening in the patterned fluoropolymer has an area in a range of $10 \, \mu m^2$ to $500 \, \mu m^2$.

39. The device according to any of embodiments 33-38 wherein the organic electrochemical transistor device comprises a plurality of independently addressable source and drain electrodes and corresponding patterned conductive polymers.

EXAMPLES

Example 1

A silicon wafer having an oxide layer was cleaned in acetone and IPA with sonication and dried. A 10% solution of Decon® 90 (comprising anionic and non-ionic surfactants) was spin applied and dried to form a very thin release layer. SU8 2050 was applied and spin coated up to 3500 rpm, baked first at 65° C. for 3 min then 95° C. for 9 min and slowly cooled to prevent thermal shock and cracking. The SU8 was about 50 μm thick. Using a shadow mask and a SUSS Micro-Tec mask aligner, the wafer was pattern exposed to i-line radiation with a total dose of 504 mJ/cm$^2$. The exposed image was similar in shape to that of part 391*a* in FIG. 13. The exposed film was given a post exposure bake at 65° C. for 2 min then 95° C. for 6 min, but not developed.

Over this structure, OSCoR 4000 photoresist (from Orthogonal, Inc.) was coated at 1500 rpm and soft baked at 90 C for 1 min. OSCoR 4000 is a photosensitive fluorinated photopolymer provided in a hydrofluoroether solvent along with a fluorinated non-ionic PAG. The fluorine content of the photosensitive fluoropolymer was about 42% by weight and the polymer included a carboxylic acid-forming precursor group. The film thickness was about 0.9 μm. Using a shadow mask and a SUSS MicroTec mask aligner, the wafer was pattern exposed to i-line radiation with a total dose of 80 mJ/cm$^2$ and given a post exposure bake of 90° C. for 1 min. This was followed by development using three (3) 30 sec puddles of Orthogonal Developer 103 (comprises a hydrofluoroether solvent that is different from the OSCoR 4000 coating solvent), each followed by spin dry step. This formed a set of open lines and pad areas of various dimensions (in this case, all >20 μm).

Following development of the OSCoR 4000, the structure was given a gentle plasma etch (100 W, 50 sccm O$_2$), followed by deposition of 10 nm Cr and then 100 nm Au. The structure was immersed in OSCoR Stripper 700 (comprising another hydrofluoroether) overnight and the photoresist and overlying metal layers were lifted off leaving patterned metal over the base layer precursor.

Next the SU8 was developed using a commercial PGMEA-based SU8 developer for 10 mins followed by a short DI water rinse which released the patterned base layer structure from the Si wafer.

Comparison 1

The steps were followed initially as in Example 1, but in place of OSCoR 4000, commercially available nLOF 2070 (AZ Electronic Materials) photoresist was used. Coating of the nLOF 2070 caused premature dissolution of the unexposed SU8 resulting in massive failure of the patterning attempt at this point. Another conventional photoresist system in the art uses a lift-off method involving bilayer of LoR5A (a polydimethylglutarimide from MicroChem) and overlying conventional photoresist. However, it was found that the LoR5A coating and lift-off solvent, NMP, rapidly dissolves unexposed SU8 and so this system is also not suitable for imaging.

Example 2

Figure 21:
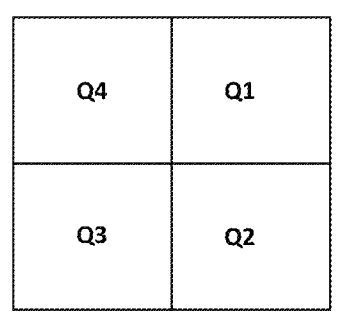

A 1.3 μm film of SU8 was prepared on a 2 cm×2 cm silicon wafer chip by spin coating SU8 3025 (diluted with cyclohexanone) at 1000 rpm, followed by a 1 min/90° C. post apply bake. The chip had four quadrants, Q1, Q2, Q3 and Q4 as shown in FIG. 21 and the SU8 was coated over all four quadrants. Next, half of the chip (quadrants Q1 and Q2) was exposed on a Pluvex 1410 UV exposure unit to a dose of 492 mJ/cm$^2$ as measured at 365 nm, followed by a 2 min PEB at 90° C.

Next a saturated solution of an organic semiconductor material, TIPS-pentacene (6,13-bis(triisopropylsilylethynyl) pentacene) in HMDSO (hexamethyldisiloxane) solvent was spin coated at 300 rpm and dried 10 sec at 90° C. to form a bluish, polycrystalline film over the SU8. OSCoR 4000 photoresist from Orthogonal, Inc. was spin coated at 1000 rpm and baked 30 sec at 90° C. to form a 1.3 μm film. Half of this photosensitive fluoropolymer was exposed (quadrants Q2 and Q3) to 200 mJ/cm$^2$, followed by a 1 min PEB at 90° C. The exposed fluoropolymer was developed with Orthogonal Developer 103 (includes a hydrofluoroether solvent) using three (3) 30 sec puddles, each followed by a spin dry step. The TIPS-pentacene was still clearly present in all areas and "uncovered" in quadrants Q1 and Q4. The uncovered TIPS-pentacene was "wet" etched by applying three (3) 15 sec puddles of HMDSO to the wafer followed by spin drying, thereby leaving TIPS-pentacene only underneath the OSCoR 4000 resist in quadrants Q2 and Q3.

Next, the SU8 was developed by applying two (2) 15 sec puddles of PGMEA solvent (which lifted off OSCoR 4000 in quadrant Q3 along with dissolving TIPS pentacene in Q3). The OSCoR 4000 was subsequently stripped using Orthogonal Stripper 700 (includes a hydrofluoroether solvent) thereby forming a patterned base layer of SU8 having a pattern corresponding to quadrants Q1 and Q2, and deposited thereon, a layer of active organic material (TIPS-pentacene) in a pattern corresponding to quadrant Q2. Rather than relying on lift off in quadrant Q3, in an alternative embodiment, the OSCoR 4000 could have instead been imaged only in quadrant Q2.

Comparison 2

The steps were followed initially as in Example 2, but in place of OSCoR 4000, commercially available nLOF 2020 (AZ Electronics Materials) photoresist was used. Coating of the nLOF caused dissolution of the TIPS-pentacene and unexposed SU8 thereby resulting in massive failure of the patterning attempt.

Example 3

A film of SU8 (2050) was spin coated and dried in a manner similar to that described Example 1 except that the substrate was a glass slide, 2.5 cm×7.5 cm. The glass slide had four quadrants similar to those described in Example 2 and FIG. 21, except the sample was rectangular rather than square. Half of the SU8 film (quadrants Q1 and Q2) was exposed to i-line UV radiation with a total dose of 550 mJ/cm$^2$. The exposed film was given a post exposure bake at 65° C. for 2 min then 95° C. for 6 min, but not developed. The SU8 surface was cleaned in a gentle O$_2$ plasma (100 W, 1 min, 50 sccm of O$_2$). A thin film of about 100 nm PEDOT:PSS was formed by spin coating (up to 4000 rpm, 40 sec) a 1% aqueous solution over the SU8, and given a post-apply bake of 90° C. for 1 min.

Over this structure, OSCoR 3313 photoresist (from Orthogonal, Inc.) was coated at 1000 rpm and soft baked at 90° C. for 20 sec. OSCoR 3313 is a photosensitive fluorinated photopolymer provided in a hydrofluoroether solvent along with a fluorinated non-ionic PAG. The fluorine content of the photosensitive fluoropolymer was about 41% by weight and the polymer included both a carboxylic acid-forming precursor group and an alcohol-forming precursor group. The film thickness was about 1.3 μm. Next, a portion of quadrant Q1 was exposed to i-line radiation with a total dose of about 72 mJ/cm$^2$ and given a post exposure bake of 90° C. for 20 sec. This was followed by development using two (2) 1 min puddles and one (1) 30 sec puddle of Orthogonal Developer 100 (comprises a hydrofluoroether solvent that is different from the OSCoR 3313 coating solvent), each followed by spin dry step.

Next, PEDOT:PSS in areas not covered by the patterned OSCoR 3313 were plasma etched (160 W, 80 sec, 50 sccm O$_2$/5 sccm CHF$_3$). PEDOT:PSS in the portion of quadrant Q1 was protected by the overlying patterned OSCoR 3313. The OSCoR 3313 was removed using Orthogonal Stripper 700 (1 min) followed by a spin dry step. Finally, the SU8 was developed using a commercial PGMEA-based SU8 developer for 15 mins, thereby forming a patterned base layer structure having an SU8 base layer in a pattern corresponding to quadrants Q1 and Q2 and having thereon a pattern of PEDOT:PSS in a portion of quadrant Q1. In an alternative embodiment, the SU8 could have instead been developed prior to stripping the OSCoR 3313.

The invention has been described in detail with particular reference to certain embodiments thereof, but it will be understood that variations, combinations, and modifications can be effected by a person of ordinary skill in the art within the spirit and scope of the invention.

LIST OF REFERENCE NUMBERS USED IN THE DRAWINGS 2 provide layer of radiation-sensitive resin step
4 form base layer precursor step
6 form first intermediate structure step
8 form second intermediate structure step
9 form patterned base layer step
20 radiation-sensitive resin
22 carrier substrate
24 release layer
40 base layer precursor
41 first pattern of exposed radiation-sensitive resin
42 second pattern of unexposed radiation-sensitive resin
45 photomask
46 radiation
60 photosensitive fluoropolymer
61 radiation
62 photomask
63 exposed layer of photosensitive fluoropolymer
64 pattern of exposed photosensitive fluoropolymer
65 pattern of unexposed photosensitive fluoropolymer
66 third pattern of fluoropolymer
67 first intermediate structure
80 material layer
81 patterned material layer
82 second intermediate structure
83 second intermediate structure
90 patterned base layer
91 patterned base layer structure
92 patterned base layer
93 patterned base layer structure
160 non-patterned fluoropolymer
161 photosensitive second polymer
163 exposed layer of photosensitive second polymer
164 pattern of exposed photosensitive second polymer
165 pattern of unexposed photosensitive second polymer
166 patterned layer of second polymer
167 first intermediate structure
168 partially patterned bilayer structure
200 secondary substrate
201 adhesion promoting layer
210 pressure
220 secondary substrate structure
260 photosensitive fluoropolymer
261 radiation
262 photomask
263 exposed layer of photosensitive fluoropolymer
264 pattern of exposed photosensitive fluoropolymer
265 pattern of unexposed photosensitive fluoropolymer
266 third pattern of fluoropolymer
267 first intermediate structure
280 material layer
281 patterned material layer
282 second intermediate structure
290 patterned base layer
291 patterned base layer structure
300 patterned base layer structure array
322 carrier substrate
324 release layer
340 base layer precursor
341 first pattern of exposed radiation-sensitive resin
342 second pattern of unexposed radiation-sensitive resin
381 electrical contact pads
382 conductive traces
383 electrode pad
384 patterned second fluoropolymer
385 modifying material
386 protective fluoropolymer layer
390 patterned base layer
391 patterned base layer structure
395 electrical contact portion
398 shank portion
482 conductive traces
484 patterned fluoropolymer
485 patterned PEDOT:PSS
490 patterned base layer
491 patterned base layer structure
497 gate electrode
498 source electrode
499 drain electrode
Q1 first quadrant of Si chip
Q2 second quadrant of Si chip
Q3 third quadrant of Si chip
Q4 fourth quadrant of Si chip

The invention claimed is:

1. A method of making a structure having a patterned base layer, comprising the steps of:
    providing a layer of a radiation-sensitive resin;
    exposing the layer of radiation-sensitive resin to patterned radiation to form a base layer precursor having a first pattern of exposed radiation-sensitive resin and a second pattern of unexposed radiation-sensitive resin;
    providing a layer of fluoropolymer in a third pattern over the base layer precursor to form a first intermediate structure;
    treating the first intermediate structure to form a second intermediate structure; and
    selectively removing either the first or second pattern of resin by contacting the second intermediate structure with a resin developing agent, thereby forming the patterned base layer.

2. The method according to claim 1 wherein the layer of radiation-sensitive resin is provided over a carrier substrate, and further comprises removal of the second intermediate structure or the patterned base layer from the carrier support.

3. The method according to claim 2 further comprising providing a release layer between the carrier support and the layer of radiation-sensitive resin, wherein the release layer promotes removal of the second intermediate structure or the patterned base layer.

4. The method according to claim 1 wherein the structure includes at least one electronic or optical feature that forms at least a portion of a transistor, a capacitor, a light-emitting device, a touch screen, a photovoltaic device, a display device, a chemical sensor, a light sensor, a bio-sensor, a bio-stimulator, a bioelectronic ion pump, an electrochemical cell, an organic electrochemical transistor, a light guide, a lens, a reflector, a color filter, a piezo device, a MEMS device or combinations thereof.

5. The method according to claim 1 wherein the patterned base layer has a Tg of 100° C. or higher.

6. The method according to claim 1 wherein the structure having a patterned base layer is one of a plurality of concurrently formed structures, each having a patterned base layer.

7. The method according to claim 6 wherein at least one of the plurality of structures has a patterned base layer in a first shape and at least one other of the plurality of structures has a patterned base layer in a second shape different from the first shape.

8. The method according to claim 1 further comprising transferring the structure to a secondary substrate.

9. The method according to claim 1 wherein the patterned base layer has an elongated shape and the structure has sufficient mechanical strength to allow insertion into biological tissue.

10. The method according to claim 9 wherein the patterned base layer has a thickness in a range of 10 to 100 μm.

11. The method according claim 1 wherein the patterned radiation causes cross-linking or polymerization in the first pattern of exposed radiation-sensitive resin, whereby contact with the resin developing agent selectively removes the second pattern of unexposed radiation-sensitive resin.

12. The method according to claim 11 wherein the fluorine content of the fluoropolymer is in a range of 15-60% by weight.

13. The method according to claim 1 wherein the third pattern of fluoropolymer is provided by:
   i) applying a composition comprising a photosensitive fluoropolymer material and a first fluorinated solvent to form a layer of photosensitive fluoropolymer;
   ii) exposing the photosensitive fluoropolymer to radiation in a pattern corresponding to the third pattern, thereby forming an exposed layer of photosensitive fluoropolymer; and
   iii) contacting the exposed layer of photosensitive fluoropolymer with a photosensitive fluoropolymer developing agent comprising at least 50% by volume of a second fluorinated solvent to selectively remove unexposed areas of the photosensitive fluoropolymer.

14. The method according to claim 13 wherein the photosensitive fluoropolymer material comprises a copolymer having at least two distinct repeating units, including a first repeating unit having a fluorine-containing group and a second repeating unit having a solubility-altering reactive group.

15. The method according to claim 13, wherein the first or second fluorinated solvent, or both, includes a hydrofluoroether.

16. The method according to claim 1 wherein the third pattern of fluoropolymer is provided by:
   a) applying a layer of non-patterned fluoropolymer over the base layer precursor, wherein the fluoropolymer is soluble in a fluorinated solvent;
   b) providing over the layer of non-patterned fluorinated polymer a layer of a second polymer in a pattern corresponding to the third pattern to form a partially patterned bilayer polymer structure, wherein the second polymer is substantially insoluble in the fluorinated solvent; and
   c) contacting the partially patterned bilayer polymer structure with the fluorinated solvent to selectively remove the fluoropolymer in areas not covered by the second polymer.

17. The method according to claim 1 wherein the treating comprises depositing a first material layer over the first intermediate structure followed by removal of the third pattern of fluoropolymer thereby forming a patterned first material layer in areas other than the third pattern.

18. The method according to claim 17 wherein the patterned first material layer forms at least a portion of an electronic or optical feature.

19. The method according to claim 1 further comprising providing a second material layer over the radiation sensitive resin and prior to providing the layer of fluoropolymer in a third pattern, and wherein the treating comprises etching the second material layer using the third pattern of fluoropolymer as an etch mask thereby forming a patterned second material layer in areas corresponding to the third pattern.

20. The method according to claim 19 wherein the second material is an organic conductor, an organic semiconductor or an organic light-emitting material.

* * * * *